(12) United States Patent
Bahnck et al.

(10) Patent No.: US 9,278,953 B2
(45) Date of Patent: Mar. 8, 2016

(54) ANTAGONISTS OF PROSTAGLANDIN EP3 RECEPTOR

(71) Applicant: Pfizer Inc., New York, NY (US)

(72) Inventors: Kevin Barry Bahnck, Old Lyme, CT (US); David James Edmonds, Arlington, MA (US); Kentaro Futatsugi, Quincy, MA (US); Esther Cheng Yin Lee, Brookline, MA (US); Alan Martin Mathiowetz, Quaker Hill, CT (US); Elnaz Menhaji-Klotz, Somerville, MA (US); Robert Vernon Stanton, Belmont, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/506,752

(22) Filed: Oct. 6, 2014

(65) Prior Publication Data

US 2015/0099782 A1    Apr. 9, 2015

Related U.S. Application Data

(60) Provisional application No. 61/888,822, filed on Oct. 9, 2013.

(51) Int. Cl.
*C07D 213/63*    (2006.01)
*A61K 31/44*    (2006.01)
*C07D 401/14*    (2006.01)

(52) U.S. Cl.
CPC .................................. *C07D 401/14* (2013.01)

(58) Field of Classification Search
None
See application file for complete search history.

(56) References Cited

FOREIGN PATENT DOCUMENTS

WO    2007027630    3/2007

OTHER PUBLICATIONS

Flesch, et al., Novel prostaglandin receptor modulators—Part II: EP receptor modulators, a patent review (2002-2012), Expert Opinion on Therapeutic Patents, vol. 23(2), pp. 233-267 (2013).
Kimple et al., "Prostaglandin E2 Receptor, EP3, Is Induced in Diabetic Islets and Negatively Regulates Glucose- and Hormone-Stimulated Insulin Secretion", Diabetes, vol. 62, pp. 1904-1912 (Jun. 2013).
Morales-Ramos et al., "Structure-activity relationship studies of novel 3-oxazolidinedione-6-naphthyl-2-pyridinones as potent and orally bioavailable EP3 receptor antagonists", Bioorganic & Medicinal Chemistry Letters, vol. 21, pp. 2806-2811 (2011).
Jin et al., "Novel 3-Oxazolidinedione-6-arylpyridinones as Potent, Selective, and Orally Active EP3 Receptor Antagonists", ACS Medicinal Chemistry Letters, vol. 1, pp. 316-320 (2010).

*Primary Examiner* — Heidi Reese
(74) *Attorney, Agent, or Firm* — Mary J. Hosley

(57) ABSTRACT

Provided herein are antagonists of prostaglandin EP3 receptor, processes to make said antagonists, and methods comprising administering said antagonists to a mammal in need thereof.

14 Claims, 2 Drawing Sheets

ANTAGONISTS OF PROSTAGLANDIN EP3 RECEPTOR

BACKGROUND OF THE INVENTION

Diabetes is a major public health concern because of its increasing prevalence and associated health risks. The disease is characterized by high levels of blood glucose resulting from defects in insulin production, insulin action, or both. Two major forms of diabetes are recognized, type I and type II. Type I diabetes develops when the body's immune system destroys pancreatic beta cells, the only cells in the body that make the hormone insulin that regulates blood glucose. To survive, people with type I diabetes must have insulin delivered by injection or a pump. Type II diabetes (T2D) accounts for about 90 to 95 percent of all diagnosed cases of diabetes. Type II diabetes usually begins as insulin resistance, a disorder in which the cells do not use insulin properly. Key target tissues, including liver, muscle, and adipose tissue, are resistant to the effects of insulin in stimulating glucose and lipid metabolism. As the need for insulin rises, the pancreas gradually loses its ability to produce insulin. Controlling type II diabetes with medication is essential; otherwise, it can progress into pancreatic beta-cell failure requiring complete dependence on insulin.

Several drugs in five major categories, each acting by different mechanisms, are available for treating hyperglycemia and subsequently, T2D (Moller, D. E., "New drug targets for Type II diabetes and the metabolic syndrome" Nature 414; 821-827, (2001)): (A) Insulin secretogogues, including sulphonyl-ureas (e.g., glipizide, glimepiride, glyburide) and meglitinides (e.g., nateglidine and repaglinide), dipeptidyl peptidease IV (DPP-IV) inhibitors (e.g., those in WO2005116014, sitagliptin, vildagliptin, alogliptin, dutogliptin, linagliptin, and saxogliptin), and glucagon-like peptide 1 (GLP-1) agonists (e.g. liraglutide, albiglutide, exenatide (Byetta®), albiglutide, lixisenatide, dulaglitide, semaglutide) enhance secretion of insulin by acting on the pancreatic beta-cells. (B) Biguanides (e.g., metformin) are thought to act primarily by decreasing hepatic glucose production. Biguanides often cause gastrointestinal disturbances and lactic acidosis, further limiting their use. (C) Inhibitors of alpha-glucosidase (e.g., acarbose) decrease intestinal glucose absorption. These agents often cause gastrointestinal disturbances. (D) Thiazolidinediones (e.g., pioglitazone, rosiglitazone) act on a specific receptor (peroxisome proliferator-activated receptor-gamma) in the liver, muscle and fat tissues. They regulate lipid metabolism subsequently enhancing the response of these tissues to the actions of insulin. Frequent use of these drugs may lead to weight gain and may induce edema and anemia. (E) Insulin is used in more severe cases, either alone or in combination with the above agents.

Ideally, an effective new treatment for T2D would meet the following criteria: (a) it would not have significant side effects including induction of hypoglycemia; (b) it would not cause weight gain; (c) it would at least partially replace insulin by acting via mechanism(s) that either increase endogenous insulin secretion or are independent from the actions of insulin; (d) it would desirably be metabolically stable to allow less frequent usage; and (e) it would be usable in combination with tolerable amounts of any of the categories of drugs listed herein. There continues to be a need for new effective treatments for T2D.

SUMMARY OF THE INVENTION

The present invention concerns compounds of Formula I that include tautomers of compounds of Formula Ia and Formula Ib:

Formula I

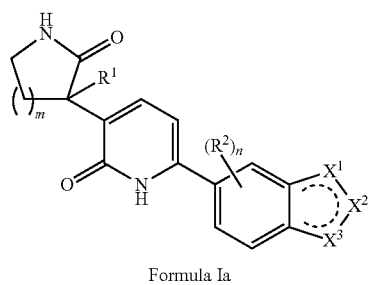

Formula Ia

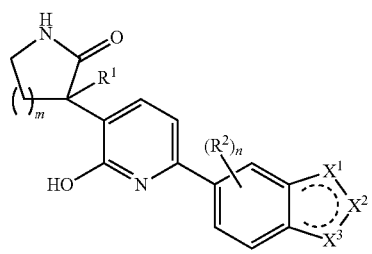

Formula Ib

The compounds of the present invention may generally be drawn as compounds of either Formula Ia or Formula Ib, but general reference to compounds of Formula I is to be understood that this representation includes both tautomers of compounds of Formula Ia and Formula Ib. However, reference to one tautomer is intended to include that one tautomer, e.g., compounds of Formula Ia, or pharmaceutically acceptable salts thereof, or, independently, compounds of Formula Ib, or pharmaceutically acceptable salts thereof.

The present invention concerns a compound of Formula I:

Formula I

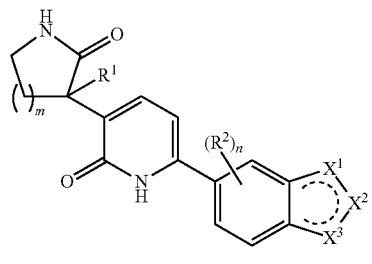

Formula Ia

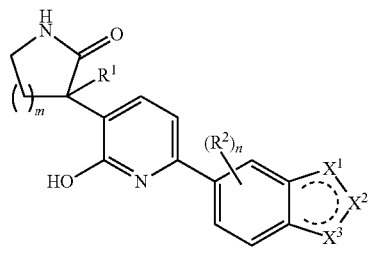

Formula Ib wherein
R¹ is H, $C_{1-6}$alkyl, or $C_{3-6}$cycloalkyl;
m is 1 or 2;
Each R² is independently halogen, $C_{1-6}$alkyl, or $C_{3-6}$cycloalkyl;
n is 0 or 1;
X¹, X², and X³ are independently =N—, —NR$^{Xn}$—, or =CR$^{Xc}$—, provided that at least 1 but no more than 2 of X¹, X², and X³ are independently =N— or —NR$^{Xn}$—;
R$^{Xn}$ is H, $C_{1-6}$alkyl, or $C_{3-6}$cycloalkyl; and
Each R$^{Xc}$ is independently H, halogen, $C_{1-6}$alkyl, or $C_{3-6}$cycloalkyl;
or a pharmaceutically acceptable salt thereof.

Another embodiment of the invention concerns a compound of Formula I, or a pharmaceutically acceptable salt thereof, as defined in any of the embodiments described herein, for use in the treatment of any one or more of bladder overactivity, cerebrovascular disease, coronary artery disease, hypertension, neurodegenerative disorders, pain, premature labor, restinosis, thrombosis, Type I Diabetes, and/or Type II diabetes.

DETAILED DESCRIPTION OF THE INVENTION

Figure 1:
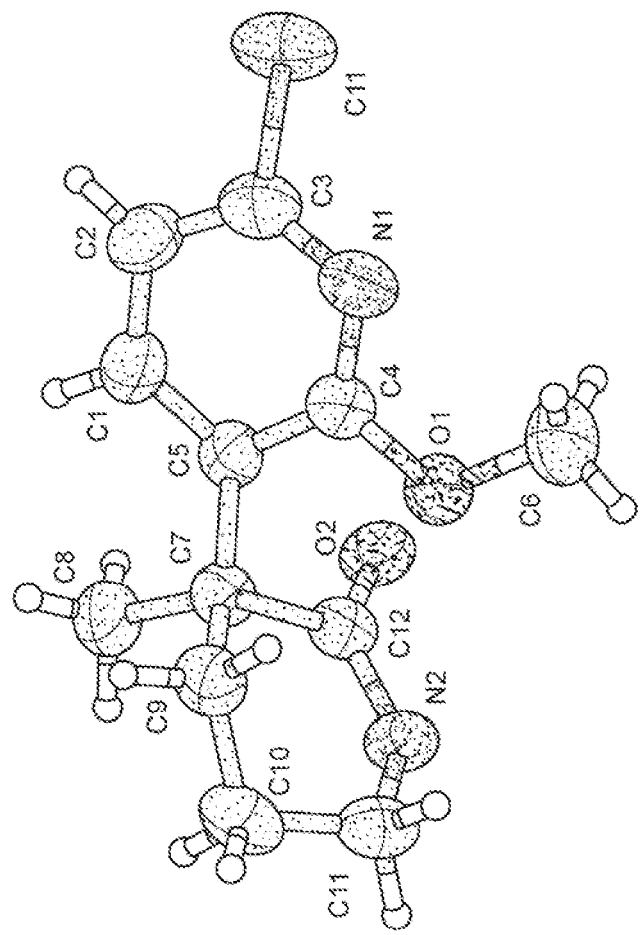
FIG. 1 is a X-ray crystal structure (ORTEP drawing) of (S)-3-(6-chloro-2-methoxypyridin-3-yl)-3-methylpiperidin-2-one.

The present invention may be understood more readily by reference to the following detailed description of exemplary embodiments of the invention and the examples included therein.

Another embodiment of the invention concerns compounds of Formula I, wherein
R¹ is H, or $C_{1-3}$alkyl;
n is 0 or 1;
R² is F, Cl, or $C_1$ alkyl;
R$^{Xn}$ is $C_{1-3}$alkyl; and
Each R$^{Xc}$ is H;
or a pharmaceutically acceptable salt thereof.

Another embodiment of the invention concerns compounds of Formula I, wherein
R¹ is H, or $C_{1-3}$alkyl;
n is 0 or 1;
R² is F, Cl, or $C_{1-3}$alkyl;
R$^{Xn}$ is $C_{1-3}$alkyl; and
Each R$^{Xc}$ is H or cyclopropyl;
or a pharmaceutically acceptable salt thereof.

Another embodiment of the invention concerns compounds of Formula I, wherein X¹, X², and X³ are independently =N—, —NR$^{Xn}$—, or =CR$^{Xc}$— to provide

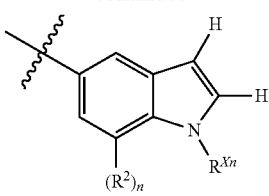

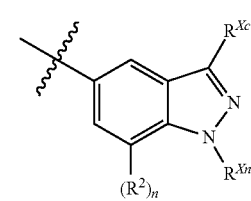

wherein n is 0 or 1;
R² is F, Cl, or $CH_3$; and
R$^{Xn}$ is $CH_3$ or $CH_2CH_3$;
R$^{Xc}$ is H, $CH_3$, $CH_2CH_3$, or cyclopropyl;
or a pharmaceutically acceptable salt thereof.

Another embodiment of the invention concerns compounds of Formula I, wherein X¹, X², and X³ are independently =N—, —NR$^{Xn}$—, or =CR$^{Xc}$— to provide

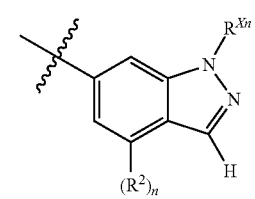

wherein n is 0 or 1;
R² is F, Cl, or $CH_3$; and
R$^{Xn}$ is $CH_3$ or $CH_2CH_3$;
or a pharmaceutically acceptable salt thereof.

Another embodiment concerns compounds of Formula I, wherein X¹, X², and X³ are independently =N—, —NR$^{Xn}$—, or =CR$^{Xc}$— to provide

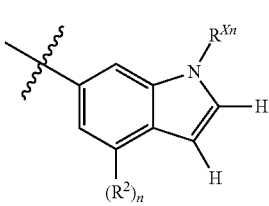

wherein n is 0 or 1;
R² is F, Cl, or $CH_3$; and
R$^{Xn}$ is $CH_3$ or $CH_2CH_3$;
or a pharmaceutically acceptable salt thereof.

Another embodiment of the invention concerns compounds of Formula I, wherein X¹, X², and X³ are independently =N—, —NR$^{Xn}$—, or =CR$^{Xc}$— to provide:

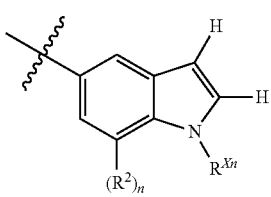

wherein n is 0 or 1;
R² is F, Cl, or CH₃; and
$R^{Xn}$ is CH₃ or CH₂CH₃;
or a pharmaceutically acceptable salt thereof.

Another embodiment of the invention concerns compounds of Formula I, wherein X¹, X², and X³ are independently =N—, —NR$^{Xn}$—, or =CR$^{Xc}$— to provide:

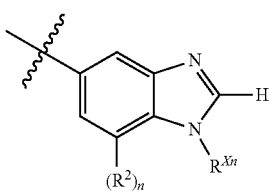

wherein n is 0 or 1;
R² is F, Cl, or CH₃; and
$R^{Xn}$ is CH₃ or CH₂CH₃;
or a pharmaceutically acceptable salt thereof.

Another embodiment of the invention concerns compounds of Formula I, wherein X¹, X², and X³ are independently =N—, —NR$^{Xn}$—, or =CR$^{Xc}$— to provide:

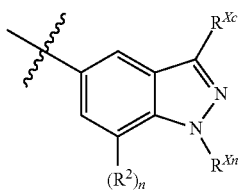

wherein n is 0 or 1;
R² is F, Cl, or CH₃; and
$R^{Xn}$ is H, CH₃ or CH₂CH₃;
$R^{Xc}$ is H, CH₃, CH₂CH₃, or cyclopropyl;
or a pharmaceutically acceptable salt thereof.

Another embodiment of the invention concerns compounds of Formula I as described herein, wherein m is 1.

Another embodiment of the invention concerns compounds of Formula I as described herein, wherein m is 2.

Another embodiment of the invention concerns compounds of Formula I as described herein, wherein n is 0.

Another embodiment of the invention concerns compounds of Formula I as described herein, wherein n is 1.

Another embodiment of the invention concerns compounds of Formula I as described herein, wherein R¹ is CH₃.

Another embodiment of the invention concerns compounds of Formula I, wherein the compound is

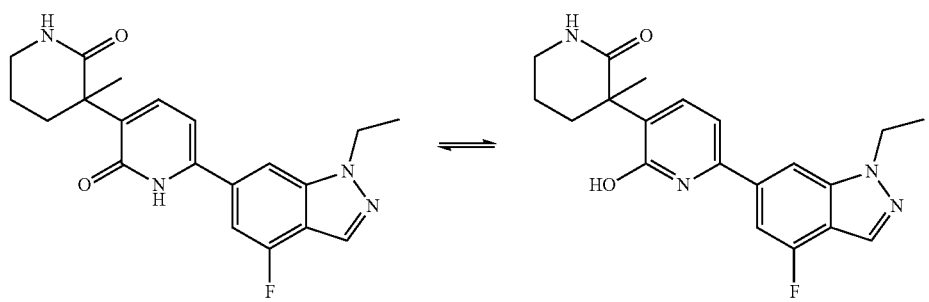

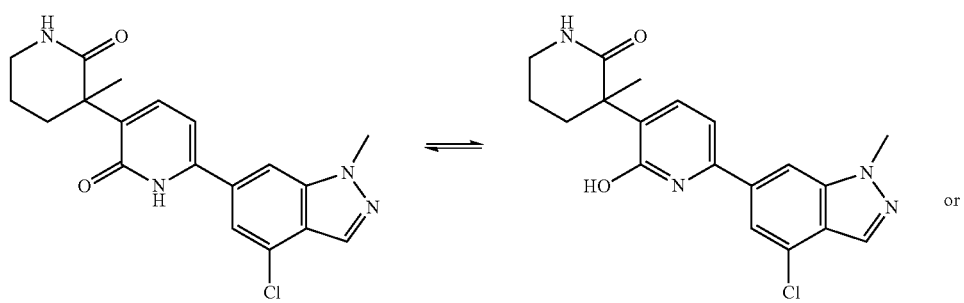

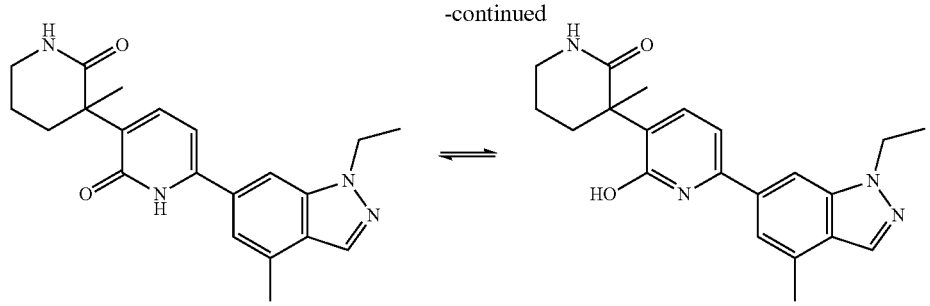
or a pharmaceutically acceptable salt thereof.
Another embodiment of the invention concerns compounds of Formula I, wherein the compound is
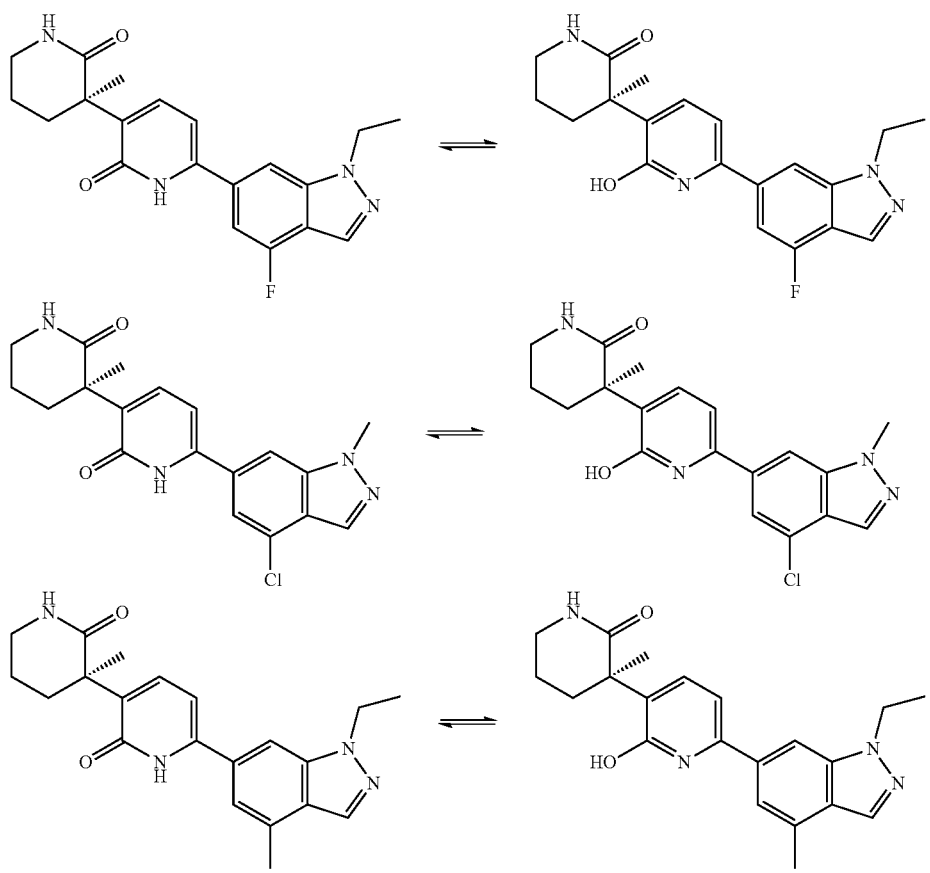
or a pharmaceutically acceptable salt thereof.
Another embodiment of the invention concerns compounds of Formula I, wherein the compound is
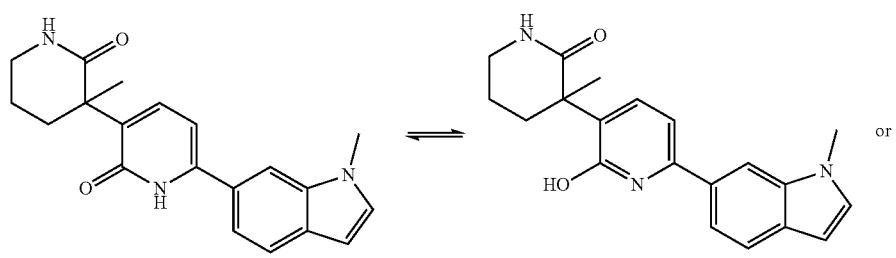
or

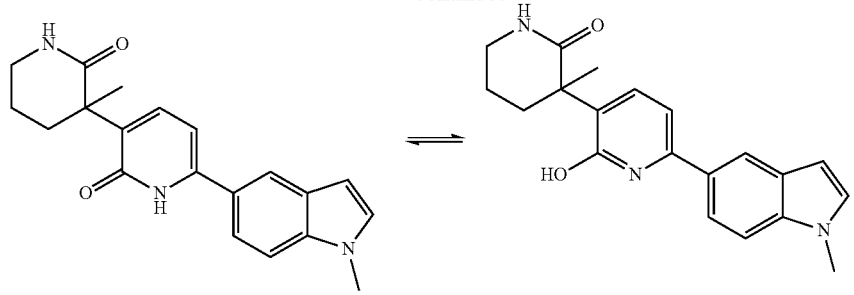
or a pharmaceutically acceptable salt thereof.
Another embodiment of the invention concerns compounds of Formula I, wherein the compound is
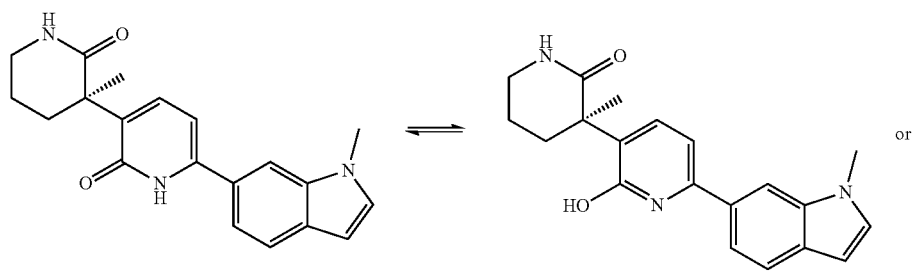
or
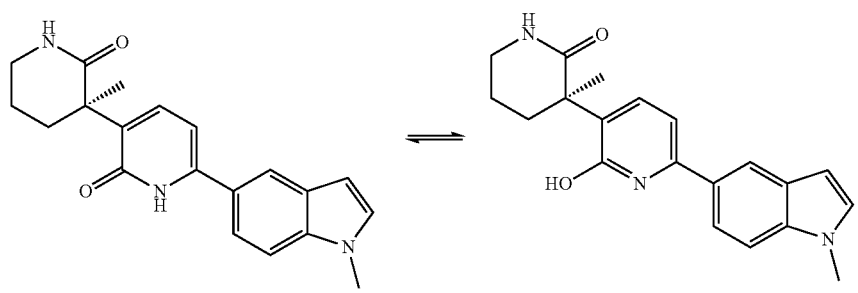
or a pharmaceutically acceptable salt thereof.
Another embodiment of the invention concerns compounds of Formula I, wherein the compound is
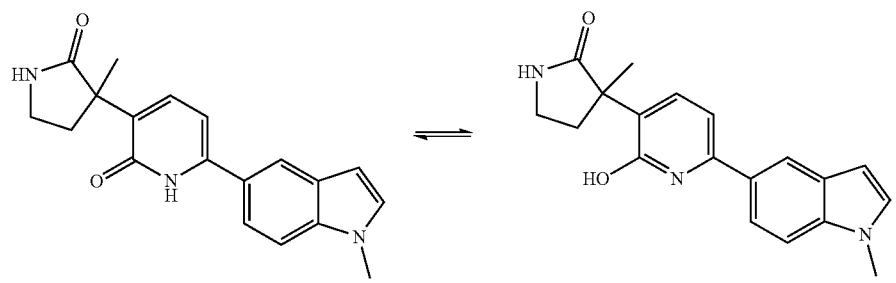 [SMILES: Cn1ccc2cc(-c3ccc(C4(C)CCNC4=O)c(=O)[nH]3)ccc21 ; Cn1ccc2cc(-c3ccc(C4(C)CCNC4=O)c(O)n3)ccc21]
or a pharmaceutically acceptable salt thereof.

Another embodiment of the invention concerns compounds of Formula I, wherein the compound is

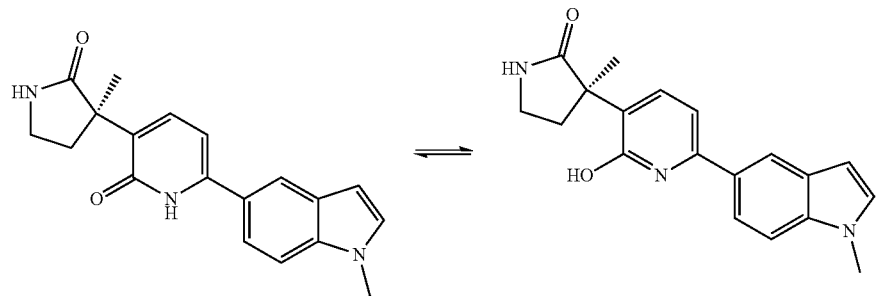 [SMILES: Cn1ccc2cc(-c3ccc([C@@]4(C)CCNC4=O)c(=O)[nH]3)ccc21 ; Cn1ccc2cc(-c3ccc([C@@]4(C)CCNC4=O)c(O)n3)ccc21]

or a pharmaceutically acceptable salt thereof.

Compounds of Formula I are tautomers between pyridinones and hydroxyl pyridines, but for ease of reference, will be referred to generally as substituted pyridinones. The invention may be understood more readily by reference to the following detailed description of exemplary embodiments of the invention and the examples presented herein. It is to be understood that this invention is not limited to specific synthetic methods of making that may of course vary. It is also to be understood that the terminology used herein is for the purpose of describing particular embodiments only and is not intended to be limiting.

As used herein, a wavy line, "⌇" denotes a point of attachment of a substituent to another group.

As used throughout this specification and the appended claims, the following terms have the following meanings:

The term "$C_{1-6}$alkyl" as used herein, means a straight or branched chain hydrocarbon containing from 1 to 6 carbon atoms. Non-limiting examples of ($C_{1-6}$)alkyl include methyl, ethyl, n-propyl, iso-propyl, n-butyl, sec-butyl, iso-butyl, tert-butyl, n-pentyl, isopentyl, neopentyl, and n-hexyl.

The term "$C_{1-3}$alkyl" as used herein, means a straight or branched chain hydrocarbon containing from 1 to 3 carbon atoms. Non-limiting examples of ($C_{1-3}$)alkyl include methyl, ethyl, n-propyl, and iso-propyl.

The term "$C_{3-6}$cycloalkyl" as used herein, means a cyclic alkyl moiety containing from 3 to 6 carbon atoms. Non-limiting examples of ($C_{3-6}$)cycloalkyl include cyclopropyl, cyclobutyl, cyclopentyl, and cyclohexyl.

The term "halogen" as used herein means chloro (Cl), fluoro (F), bromo (Br), or iodo (I).

The invention relates to a compound of Formula I, or a pharmaceutically acceptable salt thereof, used as an EP3 receptor antagonist.

The invention also relates to a compound of Formula I, or a pharmaceutically acceptable salt thereof, used as an EP3 receptor antagonist that may be used in the treatment of any one or more of the following: bladder overactivity, cerebrovascular disease, coronary artery disease, hypertension, neurodegenerative disorders, pain, premature labor, restinosis, thrombosis, Type I Diabetes, and/or Type II diabetes.

The invention also relates to (1) a compound of Formula I, or a pharmaceutically acceptable salt thereof, as defined in any of the embodiments described above, for use as a medicament; and (2) a compound of Formula I, or a pharmaceutically acceptable salt thereof, as defined in any of the embodiments described herein, for use in the treatment of any one or more of bladder overactivity, cerebrovascular disease, coronary artery disease, hypertension, neurodegenerative disorders, pain, premature labor, restinosis, thrombosis, Type I Diabetes, and/or Type II diabetes.

The present invention also provides any one or combination of:

a method of treating a disease for which an antagonist of EP3 is indicated, in a subject in need of such treatment, comprising administering to the subject a therapeutically effective amount of a compound of Formula I, or a pharmaceutically acceptable salt thereof;

the use of a compound of Formula I, or a pharmaceutically acceptable salt thereof, for the manufacture of a medicament for treating a disease or condition for which an antagonist of EP3 is indicated;

a compound of Formula I, or a pharmaceutically acceptable salt thereof, for use as a medicament;

a compound of Formula I, or a pharmaceutically acceptable salt thereof, for use in the treatment of a disease or condition for which an antagonist of EP3 is indicated;

a pharmaceutical composition comprising a compound of Formula I, or a pharmaceutically acceptable salt thereof, and a pharmaceutically acceptable excipient;

a pharmaceutical composition for the treatment of a disease or condition for which an antagonist of EP3 is indicated, comprising a compound of Formula I, or a pharmaceutically acceptable salt thereof.

The invention also relates to a pharmaceutical composition comprising a compound of Formula I, or a pharmaceutically acceptable salt thereof, as defined in any of the embodiments described herein, for use in the treatment of any one or more of the following: bladder overactivity, cerebrovascular disease, coronary artery disease, hypertension, neurodegenerative disorders, pain, premature labor, restinosis, thrombosis, Type I Diabetes, and/or Type II diabetes.

In another embodiment, the invention provides a pharmaceutical composition comprising a compound of Formula I, or a pharmaceutically acceptable salt thereof, as defined in any of the embodiments described herein, in admixture with at least one pharmaceutically acceptable excipient.

In another embodiment, the invention provides a pharmaceutical composition comprising a compound of Formula I, or a pharmaceutically acceptable salt thereof, as defined in any of the embodiments described herein, in admixture with at least one other therapeutic agent described herein.

Another embodiment of the present invention concerns all embodiments herein, wherein the compounds of Formula I are compounds of Formula Ia, or a pharmaceutically acceptable salt thereof.

Another embodiment of the present invention concerns all embodiments herein, wherein the compounds of Formula I are compounds of Formula Ib, or a pharmaceutically acceptable salt thereof.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "mammal" refers to warm blooded animals, including humans (male or female) and companion animals (e.g., dogs, cats, horses, etc.), and other animals including guinea pigs, mice, rats, gerbils, cattle, goats, sheep, monkeys, and chimpanzees.

The term "patient" is an alternative reference for mammal.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment, i.e., relieve, alleviate, or slow the progression of the patient's disease (or condition) or any tissue damage associated with the disease.

The term "antagonist" includes both full antagonists and partial antagonists, as well as inverse agonists.

As used herein, the term "Formula I" may be referred to as a "compound(s) of the invention," "the invention," and "compound of Formula I." Such terms are used interchangeably. Such terms are also defined to include all forms of the compound of Formula I, including hydrates, solvates, clathrates, isomers, crystalline (including co-crystals) and non-crystalline forms, isomorphs, polymorphs, tautomers, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereoisomers and converting (e.g. hydrolyzing) the individual diastereoisomers to the corresponding pure enantiomers. Enantiomers can also be separated by use of a chiral HPLC column. Alternatively, the specific stereoisomers may be synthesized by using an optically active starting material, by asymmetric synthesis using optically active reagents, substrates, catalysts or solvents, or by converting one stereoisomer into the other by asymmetric transformation.

Where the compounds of the present invention possess two or more stereogenic centers and the absolute or relative stereochemistry is given in the name, the designations R and S refer respectively to each stereogenic center in ascending numerical order (1, 2, 3, etc.) according to the conventional IUPAC number schemes for each molecule. Where the compounds of the present invention possess one or more stereogenic centers and no stereochemistry is given in the name or structure, it is understood that the name or structure is intended to encompass all forms of the compound, including the racemic form.

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. For example, the following is illustrative of tautomers of the compounds of Formula I.

Formula I

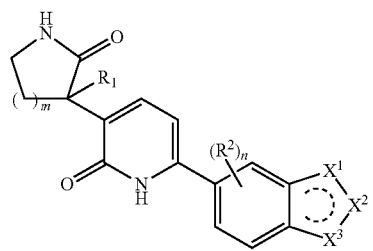

Formula Ia

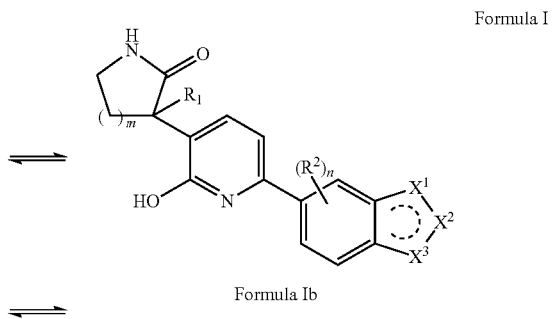

Formula Ib

The compounds of the present invention may contain asymmetric or chiral centers, and, therefore, exist in different stereoisomeric forms. Unless specified otherwise, it is intended that all stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention.

Valence tautomers include interconversions by reorganization of some of the bonding electrons.

Included within the scope of the claimed compounds of the present invention are all stereoisomers, geometric isomers and tautomeric forms of the compounds of Formula I, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

The present invention includes all pharmaceutically acceptable isotopically-labelled compounds of Formula I wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O.

Certain isotopically-labelled compounds of Formula I, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Tomography (PET) studies for examining substrate receptor occupancy.

Isotopically-labelled compounds of Formula I can generally be prepared by conventional techniques known to those skilled in the art or by processes analogous to those described in the accompanying Examples and Preparations using an appropriate isotopically-labelled reagents in place of the non-labelled reagent previously employed.

The compounds of the present invention may be isolated and used per se, or when possible, in the form of its pharmaceutically acceptable salt. The term "salts" refers to inorganic and organic salts of a compound of the present invention. These salts can be prepared in situ during the final isolation and purification of a compound, or by separately treating the compound with a suitable organic or inorganic acid or base and isolating the salt thus formed. The acids which are used to prepare the pharmaceutically acceptable acid addition salts of the aforementioned base compounds of this invention are those which form non-toxic acid addition salts, (i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, naphthylate, mesylate, glucoheptonate, lactobionate, laurylsulphonate, hexafluorophosphate, benzene sulfonate, tosylate, formate, trifluoroacetate, oxalate, besylate, palmitiate, pamoate, malonate, stearate, laurate, malate, borate, p-toluenesulfonate and pamoate (i.e. 1,1'-methylene-bis-(2-hydroxy-3-naphthoate)) salts.

The invention also relates to base addition salts of the compounds of the present invention. The chemical bases that may be used as reagents to prepare pharmaceutically acceptable base salts of those compounds of the present invention that are acidic in nature are those that form non-toxic base salts with such compounds. Such non-toxic base salts include, but are not limited to those derived from such pharmacologically acceptable cations such as alkali metal cations (e.g., lithium, potassium and sodium) and alkaline earth metal cations (e.g., calcium and magnesium), ammonium or water-soluble amine addition salts such as N-methylglucamine-(meglumine), tetramethylammonium, tetraethylammonium, methylamine, dimethylamine, trimethylamine, triethylamine, ethylamine, and the lower alkanolammonium and other base salts of pharmaceutically acceptable organic amines. See e.g. Berge, et al. *J. Pharm. Sci.* 66, 1-19 (1977).

Certain compounds of the present invention may exist in more than one crystal form (generally referred to as "polymorphs"). Polymorphs may be prepared by crystallization under various conditions, for example, using different solvents or different solvent mixtures for recrystallization; crystallization at different temperatures; and/or various modes of cooling, ranging from very fast to very slow cooling during crystallization. Polymorphs may also be obtained by heating or melting the compound of the present invention followed by gradual or fast cooling. The presence of polymorphs may be determined by solid probe NMR spectroscopy, IR spectroscopy, differential scanning calorimetry, powder X-ray diffraction or such other techniques.

In another embodiment of the present invention, a compound of Formula I may be co-administered with an anti-obesity agent where the anti-obesity agent is selected from the group consisting of gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonist (e.g., compounds described in U.S. Pat. No. 6,818,658), lipase inhibitor (e.g., Cetilistat), $PYY_{3-36}$ (as used herein "$PYY_{3-36}$" includes analogs, such as peglated $PYY_{3-36}$ e.g., those described in US Publication 2006/0178501), opioid antagonists (e.g., naltrexone), the combination of naltrexone with buproprion, oleoyl-estrone (CAS No. 180003-17-2), obinepitide (TM30338), pramlintide (Symlin®), tesofensine (NS2330), leptin, liraglutide, bromocriptine, orlistat, exenatide (Byetta®), AOD-9604 (CAS No. 221231-10-3) and sibutramine.

Other anti-obesity agents include 11β-hydroxy steroid dehydrogenase-1 (11β-HSD type 1) inhibitors, stearoyl-CoA desaturase-1 (SCD-1) inhibitor, cholecystokinin-A (CCK-A) agonists, monoamine reuptake inhibitors (such as sibutramine), sympathomimetic agents, $β_3$ adrenergic agonists, dopamine agonists (such as bromocriptine), melanocyte-stimulating hormone analogs, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-Y antagonists (e.g., NPY Y5 antagonists), thyromimetic agents, dehydroepiandrosterone or an analog thereof, glucocorticoid agonists or antagonists, orexin antagonists, glucagon-like peptide-1 agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, ghrelin antagonists, histamine 3 antagonists or inverse agonists, neuromedin U agonists, MTP/ApoB inhibitors (e.g., gut-selective MTP inhibitors, such as dirlotapide), opioid antagonist, orexin antagonist, the combination of naltrexone with buproprion and the like.

In another embodiment of the present invention, a compound of Formula I may be co-administered with an anti-diabetic agent, where the anti-diabetic agent is selected from the group consisting of an acetyl-CoA carboxylase-(ACC) inhibitor such as those described in WO2009144554, WO2003072197, WO2009144555 and WO2008065508, a diacylglycerol O-acyltransferase 1 (DGAT-1) inhibitor, such as those described in WO09016462 or WO2010086820, AZD7687 or LCQ908, monoacylglycerol O-acyltransferase inhibitors, a phosphodiesterase (PDE)-10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g. adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone and rosiglitazone), a PPAR α/γ agonist (e.g., CLX-0940, GW-1536, GW-1929, GW-2433, KRP-297, L-796449, LR-90. MK-0767 and SB-219994), a biguanide (e.g., metformin), a glucagon-like peptide 1 (GLP-1) modulator such as an agonist (e.g., exendin-3, exendin-4, ZYOG-1 and TTP273), liraglutide (Victoza®), albiglutide, exenatide (Byetta®, Bydureon®), albiglutide, lixisenatide, dulaglutide, semaglutide (NN-9924), TTP-054, a protein tyrosine phosphatase-1B (PTP-1B) inhibitor (e.g., trodusquemine, hyrtiosal extract, and compounds disclosed by Zhang, S., et al., *Drug Discovery Today*, 12(9/10), 373-381 (2007)), SIRT-1 activator (e.g., resveratrol, GSK2245840 or GSK184072), a dipeptidyl peptidease IV (DPP-IV) inhibitor (e.g., those in WO2005116014, sitagliptin, vildagliptin, alogliptin, dutogliptin, linagliptin and saxagliptin), an insulin secreatagogue, a fatty acid oxidation inhibitor, an A2 antagonist, a c-jun amino-terminal kinase (JNK) inhibitor, glucokinase activators (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g. GSK1362885), a VPAC2 receptor agonist, SGLT2 inhibitors, such as those described in E. C. Chao et al. Nature Reviews Drug Discovery 9, 551-559 (July 2010) including dapagliflozin, canagliflozin, empagliflozin, tofogliflozin (CSG452), ASP-1941, THR1474, TS-071, ISIS388626 and LX4211 as well as those in WO2010023594, a glucagon receptor modulator such as those described in Demong, D. E. et al. Annual Reports in Medicinal Chemistry 2008, 43, 119-137, GPR119 modulators, particularly agonists, such as those described in WO2010140092, WO2010128425, WO2010128414, WO2010106457, Jones, R. M. et al. in Medicinal Chemistry 2009, 44, 149-170 (e.g. MBX-2982, GSK1292263, APD597 and PSN821). FGF21 derivatives or analogs such as those described in Kharitonenkov, A. et al. et al., Current Opinion in Investigational Drugs 2009, 10(4)359-364, TGR5 (also termed GPBAR1) receptor modulators, particularly agonists, such as those described in Zhong, M., Current Topics in Medicinal Chemistry, 2010, 10(4), 386-396 and INT777. GPR40 agonists, such as those described in Medina, J. C., Annual Reports in Medicinal Chemistry, 2008, 43, 75-85, including but not limited to TAK-875, GPR120 modulators, particularly agonists, high affinity nicotinic acid receptor (HM74A) activators, and SGLT1 inhibitors, such as GSK1614235, listing of anti-diabetic agents found at page 28, line 35 through page 30, line 19 of WO2011005611, inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g. SSTR1, SSTR2, SSTR3 and SSTR5), inhibitors or modulators of PDHK2 or PDHK4, inhibitors of MAP4K4, modulators of IL1 family including IL1beta, modulators of RXRalpha, suitable antidiabetic agents include mechanisms listed by Carpino, P. A., Goodwin. B. Expert Opin. Ther. Pat, 2010, 20(12), 1627-51.

Preferred anti-diabetic agents are metformin and DPP-IV inhibitors (e.g., sitagliptin, vildagliptin, alogliptin, dutogliptin, linagliptin and saxagliptin). Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g. SSTR1, SSTR2, SSTR3 and SSTR5), inhibitors or modulators of PDHK2 or PDHK4, inhibitors of MAP4K4, modulators of IL1 family including IL1beta, modulators of RXRalpha.

In another embodiment of the present invention, a compound of Formula I may be co-administered with a cholesterol/lipid modulating agent, where the cholesterol/lipid modulating agent is selected from the group consisting of HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); HMG-CoA reductase gene expression inhibitor; squalene synthetase inhibitors; a squalene epoxidase inhibitor; a squalene cyclase inhibitor; a combined squalene epoxidase/squalene cyclase inhibitor a CETP inhibitor: fibrates; niacin, an ion-exchange resin, an antioxidant; bile acid sequestrants (such as questran); ACAT inhibitors; MTP/APO β secretion inhibitors; lipooxygenase inhibitors; cholesterol absorption inhibitors; cholesteryl ester transfer protein inhibitors; an agent such as mipomersen; and or atherosclerotic agents including PCSK9 modulators.

In another embodiment, a compound of Formula I may be co-administered with agents for the treatment of non-alcoholic steatohepatitis (NASH) and/or non-alcoholic fatty liver disease (NAFLD), such as Orlistat, TZDs and other insulin sensitizing agents, FGF21 analogs, Metformin, Omega-3-acid ethyl esters (e.g. Lovaza), Fibrates, HMG CoA-reductase Inhibitors, Ezitimbe, Probucol, Ursodeoxycholic acid, TGR5 agonists, FXR agonists, Vitamin E, Betaine, Pentoxifylline, CB1 antagonists, Carnitine, N-acetylcysteine, Reduced glutathione, lorcaserin, the combination of naltrexone with buproprion, SGLT2 Inhibitors, Phentermine, Topiramate, Incretin (GLP and GIP) analogs and Angiotensin-receptor blockers.

Additional therapeutic agents include anti-coagulant or coagulation inhibitory agents, anti-platelet or platelet inhibitory agents, thrombin inhibitors, thrombolytic or fibrinolytic agents, anti-arrythmic agents, anti-hypertensive agents, calcium channel blockers (L-type and T-type), cardiac glycosides, diruetics, mineralocorticoid receptor antagonists, NO donating agents such as organonitrates, NO promoting agents such as phosphodiesterase inhibitors, cholesterol/lipid lowering agents and lipid profile therapies, anti-diabetic agents, anti-depressants, anti-inflammatory agents (steroidal and non-steroidal), anti-osteoporosis agents, hormone replacement therapies, oral contraceptives, anti-obesity agents, anti-anxiety agents, anti-proliferative agents, anti-tumor agents, anti-ulcer and gastroesophageal reflux disease agents, growth hormone and/or growth hormone secretagogues, thyroid mimetics (including thyroid hormone receptor antagonist), anti-infective agents, anti-viral agents, anti-bacterial agents, and anti-fungal agents.

Agents used in an ICU setting are included, for example, dobutamine, dopamine, dpinephrine, nitroglycerin, nitroprusside etc.

Combination agents useful for treating vasculitis are included, for example, azathioprine, cyclophosphamide, mycophenolate, mofetil, rituximab etc.

In another embodiment, the present invention provides a combination wherein the second agent is at least one agent selected from a factor Xa inhibitor, an anti-coagulant agent, an anti-platelet agent, a thrombin inhibiting agent, a thrombolytic agent, and a fibrinolytic agent. Exemplary factor Xa inhibitors include apixaban and rivaroxaban. Examples of suitable anti-coagulants for use in combination with the compounds of the present invention include heparins (e.g., unfractioned and low molecular weight heparins such as enoxaparin and dalteparin).

In another preferred embodiment the second agent is at least one agent selected from warfarin, dabigatran, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

A preferred second agent is at least one anti-platelet agent. Especially preferred anti-platelet agents are aspirin and clopidogrel.

The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and COX-2 inhibitors such as CELEBREX or piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, PDE-III inhibitors (e.g., Pletal, dipyridamole), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticagrelor, prasugrel, ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, dabigatran, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal alpha-aminoboronic acid derivatives of lysine, omithine, arginine, homoarginine and corresponding isothiouronium analogs thereof. The term hirudin, as used herein, includes suitable derivatives or analogs of hirudin, referred to herein as hirulogs, such as disulfatohirudin. The term thrombolytics or fibrinolytic agents (or thrombolytics or fibrinolytics), as used herein, denote agents that lyse blood clots (thrombi). Such agents include tissue plasminogen activator (natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents include: Class I agents (such as propafenone); Class II agents (such as metoprolol, atenolol, carvadiol and propranolol); Class III agents (such as sotalol, dofetilide, amiodarone, azimilide and ibutilide); Class IV agents (such as ditiazem and verapamil); $K^+$ channel openers such as $I_{Ach}$ inhibitors, and $I_{Kur}$ inhibitors (e.g., compounds such as those disclosed in WO01/40231).

The compounds of the present invention may be used in combination with antihypertensive agents and such antihypertensive activity is readily determined by those skilled in the art according to standard assays (e.g., blood pressure measurements). Examples of suitable anti-hypertensive agents include: alpha adrenergic blockers; beta adrenergic blockers; calcium channel blockers (e.g., diltiazem, verapamil, nifedipine and amlodipine); vasodilators (e.g., hydralazine), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, torsemide, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g. compounds disclosed in WO 00/01389); neutral endopeptidase (NEP) inhibitors; vasopepsidase inhibitors (dual NEP-ACE inhibitors) (e.g., gemopatrilat and nitrates). An exemplary antianginal agent is ivabradine.

Examples of suitable calcium channel blockers (L-type or T-type) include diltiazem, verapamil, nifedipine and amlodipine and mybefradil.

Examples of suitable cardiac glycosides include digitalis and ouabain.

In one embodiment, a Formula I compound may be co-administered with one or more diuretics. Examples of suitable diuretics include (a) loop diuretics such as furosemide (such as LASIX™), torsemide (such as DEMADEX™), bemetanide (such as BUMEX™), and ethacrynic acid (such as EDECRIN™); (b) thiazide-type diuretics such as chlorothiazide (such as DIURIL™, ESIDRIX™ or HYDRODIURIL™), hydrochlorothiazide (such as MICROZIDE™ or ORETIC™), benzthiazide, hydroflumethiazide (such as SALURON™), bendroflumethiazide, methychlorthiazide, polythiazide, trichlormethiazide, and indapamide (such as LOZOL™); (c) phthalimidine-type diuretics such as chlorthalidone (such as HYGROTON™), and metolazone (such as ZAROXOLYN™); (d) quinazoline-type diuretics such as quinethazone; and (e) potassium-sparing diuretics such as triamterene (such as DYRENIUM™), and amiloride (such as MIDAMOR™ or MODURETIC™).

In another embodiment, a compound of Formula I may be co-administered with a loop diuretic. In still another embodiment, the loop diuretic is selected from furosemide and torsemide. In still another embodiment, one or more compounds of Formula I may be co-administered with furosemide. In still another embodiment, one or more compounds of Formula I may be co-administered with torsemide which may optionally be a controlled or modified release form of torsemide.

In another embodiment, a compound of Formula I may be co-administered with a thiazide-type diuretic. In still another embodiment, the thiazide-type diuretic is selected from the group consisting of chlorothiazide and hydrochlorothiazide. In still another embodiment, one or more compounds of Formula I may be co-administered with chlorothiazide. In still another embodiment, one or more compounds of Formula I may be co-administered with hydrochlorothiazide.

In another embodiment, one or more compounds of Formula I may be co-administered with a phthalimidine-type diuretic. In still another embodiment, the phthalimidine-type diuretic is chlorthalidone.

Examples of suitable mineralocorticoid receptor antagonists include sprionolactone and eplerenone.

Examples of suitable phosphodiesterase inhibitors include: PDE III inhibitors (such as cilostazol); and PDE V inhibitors (such as sildenafil).

Those skilled in the art will recognize that the compounds of this invention may also be used in conjunction with other cardiovascular or cerebrovascular treatments including PCI, stenting, drug eluting stents, stem cell therapy and medical devices such as implanted pacemakers, defibrillators, or cardiac resynchronization therapy.

In another embodiment, the disease and/or condition treated is selected from the group consisting of hyperlipidemia, Type I diabetes, Type II diabetes mellitus, idiopathic Type I diabetes (Type Ib), latent autoimmune diabetes in adults (LADA), early-onset Type II diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction (e.g. necrosis and apoptosis), dyslipidemia, post-prandial lipemia, conditions of impaired glucose tolerance (IGT), conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, coronary heart disease, angina pectoris, thrombosis, atherosclerosis, myocardial infarction, transient ischemic attacks, stroke, vascular restenosis, hyperglycemia, hyperinsulinemia, hyperlipidemia, hypertrygliceridemia, insulin resistance, impaired glucose metabolism, conditions of impaired glucose tolerance, conditions of impaired fasting plasma glucose, obesity, erectile dysfunction, skin and connective tissue disorders, foot ulcerations and ulcerative colitis, endothelial dysfunction and impaired vascular compliance, hyper apo B lipoproteinemia, Alzheimer's, schizophrenia, impaired cognition, inflammatory bowel disease, ulcerative colitis, Crohn's disease, and irritable bowel syndrome, non-alcoholic steatohepatitis (NASH), non-alcoholic fatty liver disease (NAFLD).

Multiple studies have demonstrated that prostaglandin E2 (PGE2) inhibits glucose-stimulated insulin secretion (GSIS) in humans. Robertson R P and Chen M (1977) *J Clin Invest* 60 747-53; Konturek S J, et al. (1978) *Prostaglandins* 15 591-602; Giugliano D et al (1983) *Am J Physiol Endocrinol Metab* 245 E591-7. The inhibition of PGE2 production has also been shown to partially restore acute GSIS, adding strength to the hypothesis that increased local production of PGE2 is a contributor to defective insulin secretion observed in diabetic patients. See infra Robertson, et al.; Chen M and Robertson R P (1978) *Diabetes* 27 750-86; McRae J R, et al. (1981) *Metabolism* 30 1065-1075; Giugliano D, et al. (1985) *J Clin Endocrinol Metab* 61 160-6. Using theophylline to maintain increased intracellular cAMP, a subsequent study confirmed that this signaling molecule was a critical component of the inhibitory action of PGE2 on GSIS. Giugliano D, et al. (1988) *Acta Endocrinologica (Copenh)* 118, 187-192. Of the four distinct receptors for the PGE2 ligand (EP1-EP4), it is therefore EP3 which has the strongest rationale as the prostanoid receptor which mediates the inhibitory effect of PGE2 on GSIS. Legler D F, et al. (2010) *Int J Biochem Cell Biol* 42 198-201. The functional link from PGE2 suppression of GSIS through EP3 has recently been confirmed using animal models and cell lines. Kimple M E, et al. (2013) *Diabetes* 62 1904-12. When taken together, these observations indicate that EP3 receptor antagonists may be useful to relieve the inhibitory action of PGE2 in diabetic patients and at least partially restore defective GSIS.

In another embodiment, the invention provides a method of affecting insulin secretion, the method comprising the administration to a mammal in need thereof a therapeutically effect amount of an EP3 antagonist. The invention further provides a method of affecting insulin secretion, the method comprising the administration to a mammal in need thereof a therapeutically effect amount of an EP3 antagonist, where the EP3 antagonist is a compound of Formula I or pharmaceutically acceptable salt thereof.

In another embodiment, the invention provides a method for treating diabetes with an antagonist of the EP3 receptor. In yet another embodiment, the invention provides a method for treating Type II diabetes with an antagonist of the EP3 receptor. Another embodiment of the invention provides a method of treating diabetes, and specifically Type II diabetes with an antagonist of the EP3 receptor, where the antagonist is a compound of Formula I, or a pharmaceutically acceptable salt thereof.

In another embodiment, the invention provides a method for treating conditions or diseases in which an antagonist of the EP3 is involved by administering a therapeutically effective amount of a compound of Formula I or a pharmaceutically acceptable salt thereof, and a pharmaceutically acceptable carrier, to a mammal in need thereof. In another embodiment, the invention provides a method for treating conditions or diseases in which an antagonist of the EP3 is involved by administering a therapeutically effective amount of any embodiment of a compound of Formula I or a pharmaceutically acceptable salt thereof, and a pharmaceutically acceptable carrier, to a mammal in need thereof. Non-limited examples of such conditions or diseases include any one or combination of the following: bladder overactivity, cerebrovascular disease, coronary artery disease, hypertension, neurodegenerative disorders, pain, premature labor, restinosis, thrombosis, Type I Diabetes, and/or Type II diabetes.

In another embodiment, the invention provides combination therapies wherein the compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided.

Combination Agents

The compounds of the present invention may be used, alone or in combination with other therapeutic agents, in the treatment of various conditions or disease states. The compound(s) of the present invention and other therapeutic agent(s) may be administered simultaneously (either in the same dosage form or in separate dosage forms) or sequentially.

The administration of two or more compounds "in combination" means that the two compounds are administered closely enough in time that the presence of one alters the biological effects of the other. The two or more compounds may be administered simultaneously, concurrently or sequentially. Additionally, simultaneous administration may be carried out by mixing the compounds prior to administration or by administering the compounds at the same point in time but as separate dosage forms at the same or different site of administration.

In another embodiment, the compounds of this invention are co-administered with any one or more additional therapeutic agent(s) as described herein. The combination agents are administered to a mammal in a therapeutically effective amount to treat the diseases and/or condition described herein, e.g., obesity, diabetes, and cardiovascular conditions such as anti-hypertensive agents and coronary heart disease.

The phrases "concurrent administration," "co-administration," "simultaneous administration," and "administered simultaneously" mean that the compounds are administered in combination.

Kits

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

In another embodiment, the invention relates to the novel intermediates useful for preparing the compounds of the invention.

Administration and Dosing

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts.

The compounds of the invention may be administered orally. Oral administration may involve swallowing, so that the compound enters the gastrointestinal tract, or buccal or sublingual administration may be employed by which the compound enters the bloodstream directly from the mouth.

In another embodiment, the compounds of the invention may also be administered directly into the bloodstream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing 0.01, 0.05, 0.1, 0.5, 1.0, 2.5, 5.0, 10.0, 15.0, 25.0, 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.01 to about 10 mg/kg/minute during a constant rate infusion.

Suitable subjects according to the present invention include mammalian subjects. Mammals according to the present invention include canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

Pharmaceutical Compositions

For the treatment of the diseases or conditions referred to herein, the compounds of the invention may be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of Formula I are ordinarily combined with one or more adjuvants. Such capsules or tablets may contain a controlled release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (i.e., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneally, intramuscular injections, intrasternal injections, and infusion. Injectable preparations (i.e., sterile injectable aqueous or oleaginous suspensions) may be formulated according to the known art using suitable dispersing, wetting agents, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, B. C. Finnin and T. M. Morgan, J. Pharm. Sci., vol. 88, pp. 955-958, 1999.

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (i.e., absorbable gel sponges, collagen) and non-biodegradable (i.e., silicone) implants, wafers, lenses and particulate or vesicular systems, such as niosomes or liposomes. A polymer such as crossed linked polyacrylic acid, polyvinyl alcohol, hyaluronic acid, a cellulosic polymer, for example, hydroxypropylmethylcellulose, hydroxyethylcellulose, or methylcellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover. John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients (3rd Ed.), American Pharmaceutical Association, Washington, 1999.

EXAMPLES

Compounds of the present invention may be synthesized by the methods described below, together with synthetic routes that include processes analogous to those well-known in the chemical arts, or modifications and transformations that are familiar to those of ordinary skill in the art, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, New York (1967-1999 ed.), or *Beilsteins Handbuch der oraanischen Chemie*, 4, Aufl. ed. Springer-Verlag, Berlin, including supplements (also available via the Beilstein online database)). Many of the compounds used herein, are related to, or are derived from compounds in which there is a large scientific interest and commercial need, and accordingly many such compounds are commercially available or are reported in the literature or are easily prepared from other commonly available substances by methods which are reported in the literature.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of Formula I, or their pharmaceutically acceptable salts, can be prepared according to the reaction Examples discussed herein. Isolation and purification of the products is accomplished by standard procedures, which are known to a chemist of ordinary skill. It will be apparent to one skilled in the art that all of the synthetic transformations can be conducted in a precisely similar manner whether the materials are enantioenriched or racemic. Moreover the resolution to the desired optically active material may take place at any desired point in the sequence using well known methods such as described herein and in the chemistry literature.

The following represent abbreviations for chemicals, solvents and reagents used in this document:

"DMSO" refers to dimethylsulfoxide, "DCE" refers to dichloroethane, "DMF" refers to dimethylforamide, "EtOAc" refers to ethyl acetate. "EtOH" refers to ethanol. "MeOH" refers to methanol, "MeCN" refers to acetonitrile, "$CH_2Cl_2$" refers to methylene chloride, "DCM" refers to methylene chloride (dichloromethane), "NMP" refers to N-methyl-2-pyrrolidone, "PE" refers to petroleum ether, "MTBE" refers to methyl tert-butyl ether, "THF" refers to tetrahydrofuran, "KOAc" refers to potassium acetate, "KHMDS" refers to potassium bis(trimethylsilyl)amide, "LiHMDS" refers to lithium bis(trimethylsilyl)amide, "MeI" refers to methyl iodide, "NaOtBu" refers to sodium tert-butoxide, "$PtO_2$" refers to platinum oxide, "Pd(dppf)$Cl_2$" refers to [1,1'-bis(diphenylphosphino)ferrocine]dichloropalladium(II) (1:1), "tert-BuLi" refers to tert-butyllithium, "TsOH.H2O" refers to p-toluenesulfonic acid monohydrate, "TMSCl" refers to trimethylsilyl chloride, "BSA" refers to bovine serum albumin, "aq." refers to aqueous.

The following abbreviations include units. The term "room temperature" and/or "r.t." refers to a temperature between 18 to 25° C. and "° C." refers to degrees Celsius. "nm" refers to nanometer, "mm" refers to millimeter, "μm" refers to micrometer, "pM" refers to picomolar, "μM" refers to micromolar, "mM" refers to millimolar, "M" refers to molar, "mmol" refers to millimole, "μg" refers to microgram, "mg" refers to milligram, "g" refers to gram, "μL" refers to microliter, "mL" refers to milliliter, "Psi" refers to pounds per square inch, "h" refers to hour, "min." refers to minute, "w/v" refers to mass concentration (mass/volume).

The following abbreviations address spectroscopy. "NMR" refers to nuclear magnetic resonance spectroscopy, "CDCl$_3$" refers to deuterated chloroform, "MHz" refers to megahertz, "s" refers to singlet, "d" refers to doublet, "t" refers to triplet, "q" refers to quartet, "dd" refers to doublet of doublets, "ddd" refers to doublet of doublet of doublets, "td" refers to triplet of doublets, "dt" refers to doublet of triplets, "br.s." refers to broad singlet, "m" refers to multiplet, "H" refers to proton, "MS" refers to mass spectrometry, "ES" refers to electron scatter, "AP" refers to atmospheric pressure, "SFC" refers to super critical chromatography, "$CO_2$" refers to carbon dioxide, "HPLC" refers to high pressure liquid chromatography, "MPLC" refers to medium pressure liquid chromatography, "TLC" refers to thin layer chromatography, "ORTEP" refers to Oak Ridge Thermal-Ellipsoid Plot.

Other abbreviations include the following. "$K_d$" refers to dissociation constant, "$K_i$" refers to enzyme inhibitor constant, "$IC_{50}$" refers to half maximal inhibitory concentration. "SPA" refers to Scintillation proximity assay. "WGA" refers to Wheat Germ Agglutinin. "PVT" refers to Polyvinyltoluene.

Experiments were generally carried out in air or, under an inert atmosphere (nitrogen or argon), particularly in cases where oxygen- or moisture-sensitive reagents or intermediates were employed. Concentration in vacuo means that a rotary evaporator was used. Unless otherwise noted, chemical reactions were performed at room temperature (18-25° C.).

Commercial solvents and reagents were generally used without further purification, including anhydrous solvents where appropriate (generally Sure-Seal™ products from the Aldrich Chemical Company, Milwaukee, Wis.). Reaction progress was monitored using thin layer chromatography (TLC), liquid chromatography-mass spectrometry (LCMS), high performance liquid chromatography (HPLC), and/or gas chromatography-mass spectrometry (GCMS) analyses. Products were generally dried under vacuum before being carried on to further reactions or submitted for biological testing. Proton nuclear magnetic spectroscopy ($^1$H NMR) was recorded with 400, 500 or 600 MHz spectrometers. Chemical shifts are expressed in parts per million (ppm, δ) referenced to residual peaks from the deuterated solvents employed. The peak shapes are denoted as follows: s, singlet; d, doublet; t, triplet; q, quartet; m, multiplet; br. s, broad singlet; br. m, broad multiplet. Mass spectrometry (MS) data is reported from either liquid chromatography-mass spectrometry (LCMS) or gas chromatography-mass spectrometry (GCMS) instrumentation via atmospheric pressure chemical ionization (APCI) or electron scatter (ES) ionization sources. Silica gel chromatography was performed primarily using a medium pressure system using columns pre-packaged by various commercial vendors. Microanalyses were performed by Quantitative Technologies Inc. and were within 0.4% of the calculated values.

The terms "concentrated" and "evaporated" refer to the removal of solvent at reduced pressure on a rotary evaporator with a bath temperature less than 60° C. Unless indicated otherwise, percent is percent by weight given the component and the total weight of the composition, temperature is in ° C. or is at ambient temperature, and pressure is at or near atmospheric. Room or ambient temperature refers to 18-25° C.

The compounds and intermediates described below were named using the naming convention provided with ChemBioDraw Ultra, Version 12.0 (CambridgeSoft Corp., Cambridge, Mass.). The naming convention provided with ChemBioDraw Ultra, Version 12.0 are well known by those skilled in the art and it is believed that the naming convention provided with ChemBioDraw Ultra, Version 12.0 generally comports with the IUPAC (International Union for Pure and Applied Chemistry) recommendations on Nomenclature of Organic Chemistry and the CAS Index rules.

For syntheses referencing procedures in other Examples or Methods, reaction conditions (length of reaction and temperature) may vary. Purifications may vary between experiments: in general, solvents and the solvent ratios used for eluents/gradients were chosen to provide appropriate Rfs or retention times.

Intermediates (R)-3-(6-chloro-2-methoxypyridin-3-yl)-3-methylpiperidin-2-one

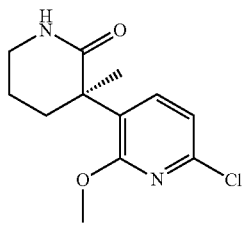 [SMILES: COc1nc(Cl)ccc1[C@@]1(C)CCCNC1=O]

Step 1:
2-(6-Chloro-2-methoxypyridin-3-yl)propanenitrile

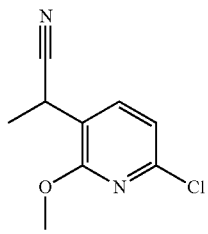

To a suspension of 3-bromo-6-chloro-2-methoxypyridine (99.9 g, 449 mmol), [1,1'-Bis(diphenylphosphino)ferrocene]dichloropalladium(II) complex with dichloromethane (2.76 g, 3.38 mmol), and NaOtBu (105 g, 1090 mmol) in dioxane (805 mL) was added tert-butyl cyanoacetate (64.8 mL, 454 mmol) under nitrogen. The reaction mixture was heated for 235 min while maintaining the internal reaction temperature at 75° C. under nitrogen. After being cooled to 20° C., to the reaction mixture was added MeI (55.9 mL, 898 mmol) in one portion, and the resulting mixture was stirred overnight at r.t. Celite® (24 g) was added to the reaction mixture, and the resulting mixture was filtered through a 370 g silica plug. The plug was eluted with EtOAc/heptanes (1/3, 2.0 L), and the combined filtrate was concentrated. A solution of the crude residue (133.9 g) in DMSO (330 mL) and water (67 mL) was heated at 130° C. for 15.8 h. The reaction mixture was filtered through a plug of Celite®, and the filter cake was rinsed with MTBE and water. The filtrate was filtered again through a plug of Celite® and the filter cake was washed with MTBE and water. The filtrate was partitioned between MTBE (total volume=2.0 L), water (total volume=1.0 L) and brine (100 mL). The layers were separated and the organic layer was washed with water (1.0 L) and brine (750 mL), dried over $Na_2SO_4$, and concentrated to afford the crude 2-(6-Chloro-2-methoxypyridin-3-yl)propanenitrile (87.6 g, 99%) as a dark brown oil, which was used for the next step without any further purification. $^1$H NMR (600 MHz, $CDCl_3$) δ 1.58 (d, 3H), 4.01 (s, 3H), 4.11 (q, 1H), 6.97 (d, 1H), 7.66 (d, 1H). MS (ES+)(M+H) 197.

Step 2: (R)-3-(6-chloro-2-methoxypyridin-3-yl)-3-methylpiperidin-2-one

A solution of crude 2-(6-chloro-2-methoxypyridin-3-yl)propanenitrile (25.9 g, 132 mmol) and tert-butyl 2,2-dioxooxathiazinane-3-carboxylate (45.8 g, 193 mmol) in THF (440 mL), under nitrogen, was cooled in an ice/water bath for 10 min. To this solution was added a solution of KHMDS in THF (1.0 M, 255 mL, 260 mmol) over 25 min, while maintaining internal reaction temperature at or below 20° C. After continued stirring for 15 min and with the cold bath still present, conc. HCl aq. (91 mL) was added cautiously in one portion, and the resulting mixture was stirred for 10 min. The reaction mixture was then heated to reflux for 2.3 h. Cooling with an ice/water bath was commenced, and, when the internal temperature reached 24° C., the reaction was quenched by portionwise addition of a saturated aqueous solution of ammonia (70 mL). Volatile components were removed under reduced pressure, and the residue was partitioned between EtOAc (1.0 L) and 5% (w/v) aq. sodium carbonate (600 mL). The aqueous layer was extracted with EtOAc (500 mL), and the combined organic extracts were dried over $Na_2SO_4$ and concentrated under reduced pressure to afford crude residue as a dark red-brown oil (33.84 g). To a solution of the residue (33.3 g) in MeOH (310 mL) was added a 4.5 M aqueous solution of KOH. The reaction was then heated to reflux for 8.5 h. Heating was continued, at this point, with a distillation head for 2.2 h, collecting a total of ca. 175 mL of distillate. Reflux was then resumed for an additional 1.5 h, whereupon it was cooled to r.t. and concentrated under reduced pressure to remove its low-boiling components. Phosphoric acid (85%, 24 mL) was added to the resulting suspension, and solids were collected by vacuum filtration after thorough mixing. This material was washed with several small portions of water and azeotropically dried by evaporation from MeCN to afford a crude 3-(6-chloro-2-methoxypyridin-3-yl)-3-methylpiperidin-2-one as a tan-brown solid (15.3 g, 46%), which was ca. 90% pure. $^1$H NMR (600 MHz, $CDCl_3$) δ 1.58-1.64 (m, 1 H), 1.66 (s, 3 H), 1.76-1.82 (m, 1 H), 1.92-2.01 (m, 1H), 2.26 (td, 1 H), 3.35-3.42 (m, 1 H), 3.47 (td, 1 H), 3.97 (s, 3 H), 5.91 (br. s., 1 H), 6.91 (d, 1 H), 7.53 (d, 1 H).

Two enantiomers of 3-(6-chloro-2-methoxypyridin-3-yl)-3-methylpiperidin-2-one were separated via chiral preparative SFC.

Peak 1
Analytical chiral SFC retention time of 5.679 min (Method: Column: Phenomenex Lux Amylose-2, 4.6 mm×250 mm, 5 μm; Mobile Phase A: CO₂, Mobile Phase B: Methanol+0.2% Ammonia; Gradient: Hold 95% A for 1.5 min, then a linear gradient from 95% A to 40% A over 9 min, hold 40% A for 1.0 min, then equilibrate column at 95% A for 1.0 min. Flow: 3 mL/min; Backpressure 120 Bar; Column Temperature: 40° C.; UV detection 210 nm).

Preparative conditions are as follows: Column: Phenomenex Lux Amylose-2 21.2 mm×500 mm, 5 μm; Isocratic mobile phase: 80% CO₂: 20% Methanol+0.2% Ammonia; Backpressure: 120 Bar; Flow: 80 mL/min, System temperature 40° C.; UV detection 210 nm.

The absolute configuration of this enantiomer was assigned by X-ray crystallography. The crystal used for the X-ray crystallography was obtained from DCE/heptanes, using the following vapor diffusion procedure: A one dram vial was charged with 20 mg of 6-chloro-2-methoxypyridin-3-yl)-3-methylpiperidin-2-one (Peak 1), and this material was dissolved in minimal dichloroethane (ca. 400 μL) to obtain a homogeneous solution. This open one dram vial was placed inside a 20 mL scintillation vial containing a charge of heptane (ca. 3 mL). The outer vial was sealed, and vapour diffusion was allowed to occur over 5 days. Single crystals were removed from the inner vial with a spatula, rinsed with heptane, and analyzed by X-ray crystallography. FIG. 1 is an ORTEP drawing of (S)-3-(6-chloro-2-methoxypyridin-3-yl)-3-methylpiperidin-2-one. Single Crystal X-Ray Analysis for (S)-3-(6-chloro-2-methoxypyridin-3-yl)-3-methylpiperidin-2-one: Data collection was performed on a Bruker APEX diffractometer at room temperature.

The structure was solved by direct methods using SHELX software suite in the space group P2₁. The structure was subsequently refined by the full-matrix least squares method. All non-hydrogen atoms were found and refined using anisotropic displacement parameters. The structure was solved with five molecules in the asymmetric unit, with a half-occupied disordered solvate. All hydrogen atoms were placed in calculated positions and were allowed to ride on their carrier atoms. The final refinement included isotropic displacement parameters for all hydrogen atoms. Analysis of the absolute structure using likelihood methods (R. W. W. Hooft et al. *J. Appl. Cryst.* (2008), 41, 96-103) was performed using PLATON (A. L. Spek, *J. Appl. Cryst.* (2003), 36, 7-13). The final R-index was 5.5%. A final difference Fourier revealed no missing or misplaced electron density, aside from a few higher than normal residuals near the half occupied solvate. Pertinent crystal, data collection and refinement of (S)-3-(6-chloro-2-methoxypyridin-3-yl)-3-methylpiperidin-2-one are summarized in Table 1, and graphically presented in FIG. 1.

TABLE 1

Crystal data and structure refinement for Empirical formula C124 H140 Cl10 N20 O21

| | |
|---|---|
| Formula weight | 2601.06 |
| Temperature | 273(2) K |
| Wavelength | 1.54178 Å |
| Crystal system | Monoclinic |
| Space group | P2(1) |
| Unit cell dimensions | a = 12.4551(9) Å    α = 90°. |
| | b = 11.7120(9) Å    β = 92.151(3)°. |
| | c = 24.2745(18) Å   γ = 90°. |
| Volume | 3538.5(5) Å³ |
| Z | 1 |
| Density (calculated) | 1.221 Mg/m³ |

Peak 2

Base on the X-ray analysis of peak 1, which was assigned as (S)-enantiomer, peak 2 was assigned as (R)-enantiomer. Analytical SFC retention time 6.478 min (preparative and analytical methods same as for peak 1 above). ¹H NMR (600 MHz, CDCl₃) δ 1.61-1.63 (m, 1H), 1.67 (s, 3H), 1.77-1.83 (m, 1H), 1.95-2.01 (m, 1H), 2.26 (td, 1H), 3.39-3.41 (m, 1H), 3.48 (td, 1H), 3.88 (s, 3H), 6.06 (brs, 1H), 6.92 (d, 1H), 7.54 (d, 1H). MS (AP+)(M+H) 255.

Alternative Synthesis of 3-(6-chloro-2-methoxypyridin-3-yl)-3-methylpiperidin-2-one Step 1: Methyl 2-(6-chloro-2-methoxypyridin-3-yl)propanoate

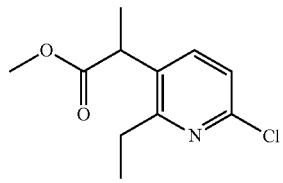

To a stirred solution of 2-(6-Chloro-2-methoxypyridin-3-yl)propanenitrile (1850 g, 9439 mmol) in MeOH (20 L) was added MeOH/HCl (about 2 M) at r.t. After the addition, the resulting mixture was heated at reflux for 12 hours. The reaction mixture was evaporated to move most of MeOH, and the residue was diluted with H₂O (6 L) and basified to pH=9~10 with solid NaHCO₃. The aqueous layer was extracted with CH₂Cl₂ (15 L). The organic layer was washed with water (10 L) and brine (10 L), dried over Na₂SO₄ and concentrated to dryness. The crude residue was purified by column chromatography (petroleum ether/EtOAc=100: 0~80:20) to afford methyl 2-(6-chloro-2-methoxypyridin-3-yl)propanoate (1450 g, 67%) as a yellow oil. ¹H NMR (400 MHz, CDCl₃) δ 1.44 (d, 3H), 3.67 (s, 3H), 3.91 (q, 1H), 3.95 (s, 3H), 6.89 (d, 1H), 7.45 (d, 1H).

Step 2: Methyl 2-(6-chloro-2-methoxypyridin-3-yl)-4-cyano-2-methylbutanoate

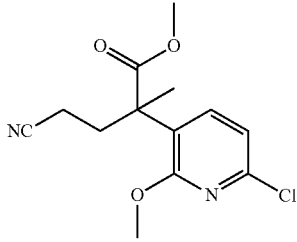 [SMILES: COC(=O)C(C)(CCC#N)c1ccc(Cl)nc1OC]

This reaction was carried out in 22 batches.

To a solution of methyl 2-(6-chloro-2-methoxypyridin-3-yl)propanoate (100 g, 435 mmol) in THF (1.5 L) was added LiHMDS (609 mL, 609 mmol) dropwise over a period of 60 min at −60° C. while maintaining reaction temperature below −50° C. After the addition, the reaction mixture was stirred below −50° C. for 30 min. Then a solution of 3-bromopropanenitrile (92 g, 697 mmol) in THF (0.4 L) was added dropwise to above solution below −50° C. over a period of 90 min. The resulting mixture was stirred at r.t. for 16 hours. The reaction mixture was quenched with saturated aqueous NH₄Cl (500 mL) below 25° C. The 22 batches were combined for workup together. The mixture was diluted with H₂O (15 L), and extracted with EtOAc (15 L). The combined organic layers were washed with water (15 L) and brine (15 L), dried over Na₂SO₄ and concentrated to dryness. The crude residue was purified by column chromatography (petroleum ether/EtOAc=100:0~80:20) to give methyl 2-(6-chloro-2-methoxypyridin-3-yl)-4-cyano-2-methylbutanoate (1100 g, 41%) as a colorless oil. ¹H NMR (400 MHz, CDCl₃) δ 1.56 (s, 3H), 2.16-2.33 (m, 3H), 2.35-2.47 (m, 1H), 3.65 (s, 3H), 3.93 (s, 3H), 6.96 (d, 1H), 7.44 (d, 1H).

Step 3: 3-(6-chloro-2-methoxypyridin-3-yl)-3-methylpiperidin-2-one

This reaction was carried out in 12 batches.

To a stirred solution of methyl 2-(6-chloro-2-methoxypyridin-3-yl)-4-cyano-2-methylbutanoate (110 g, 390 mmol) and conc. HCl (60 mL) in MeOH (1 L) was added PtO₂ (11 g) under N₂. The suspension was degassed and refilled with H₂ several times. Then the resulting mixture was stirred under 50 Psi of H₂ at r.t for 16 hours. The reaction mixture was filtered and the combined filtrates were evaporated to dryness. To the above residue in MeOH (12 L) was added solid K₂CO₃ (2158 g, 15.6 mol) at r.t. The reaction mixture was heated at reflux for 16 hours. The reaction mixture was filtered, and the filter cake was washed with MeOH (5 L). The combined filtrates were evaporated to dryness, and the crude residue was partitioned between CH₂Cl₂ (10 L) and water (5 L). The aqueous layer was extracted with CH₂Cl₂ (5 L). The combined organic layers were washed with brine (5 L), dried over Na₂SO₄ and concentrated to dryness. The crude residue was triturated with MTBE to give 3-(6-chloro-2-methoxypyridin-3-yl)-3-methylpiperidin-2-one (770 g, 64%) as a white solid. ¹H NMR was consistent with data described in the other synthetic route.

(R)-3-(6-chloro-2-methoxypyridin-3-yl)-3-methylpyrrolidin-2-one

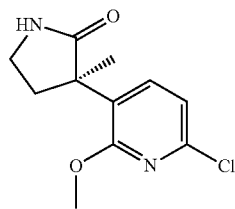 [SMILES: COc1nc(Cl)ccc1[C@@]1(C)CCNC1=O]

Step 1: Ethyl 2-(6-chloro-2-methoxypyridin-3-yl)-2-hydroxypropanoate

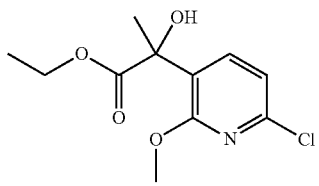 [SMILES: CCOC(=O)C(C)(O)c1ccc(Cl)nc1OC]

The reaction was carried out on 4 batches in parallel and workup together.

To a solution of 2-chloro-6-methoxypyridine (100 g, 696 mmol) in anhydrous THF (1.0 L) was added a solution of tert-BuLi in pentane (1.3 M, 640 mL, 836 mmol) at −68° C. dropwise. The reaction mixture was stirred for 30 min at this temperature. To the reaction mixture was added a solution of ethyl glyoxalate (109 g, 940 mmol) in THF (400 mL) was added dropwise below −60° C. over 1.5 h, and the resulting mixture was stirred at this temperature for 1 h. The reaction mixture was poured into ice water (10 L), extracted with EtOAc (10 L), dried over Na₂SO₄, and concentrated. The crude product was purified by silica gel column chromatography (petroleum ether→petroleum ether EtOAc=5:1) to afford ethyl 2-(6-chloro-2-methoxypyridin-3-yl)-2-hydroxypropanoate (360 g, 50%) as a yellow oil. ¹H NMR (400 MHz, CDCl₃) δ 1.20 (t, 3H), 1.75 (s, 3H), 3.95 (s, 3H), 4.20 (q, 2H), 6.95 (d, 1H), 7.67 (d, 1H).

Step 2: Ethyl 2-(6-chloro-2-methoxypyridin-3-yl)acrylate

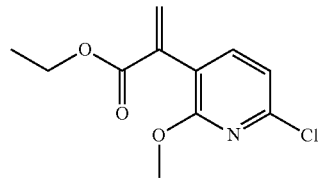 [SMILES: C=C(C(=O)OCC)c1ccc(Cl)nc1OC]

The reaction was carried out on 2 batches in parallel and workup together.

A mixture of ethyl 2-(6-chloro-2-methoxypyridin-3-yl)-2-hydroxypropanoate (220 g, 847 mmol) and TsOH·H₂O (80.5 g, 423 mmol) in dry toluene (1.5 L) was heated at reflux azeotropically with a Dean-Stark trap for 5 h. All of reaction solutions were combined together for work up. After being cooled, the combined reaction mixtures were washed with 10% Na₂CO₃ aq., and the aqueous layer was extracted with EtOAc. The combined organic extracts were washed with brine, dried over Na₂SO₄ and concentrated to afford ethyl 2-(6-chloro-2-methoxypyridin-3-yl)acrylate (368 g 90%) as a black oil, which was used for next step without any further purifications.

Step 3: Ethyl 2-(6-chloro-2-methoxypyridin-3-yl)propanoate

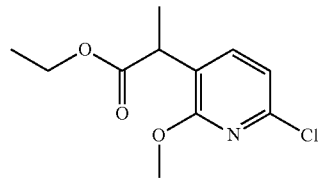 [SMILES: CCOC(=O)C(C)c1ccc(Cl)nc1OC]

To a solution of crude ethyl 2-(6-chloro-2-methoxypyridin-3-yl)acrylate (203 g, 0.84 mol) in MeOH (2 L) was added NaBH₄ (63.8 g, 1.68 mol) in portions at 0° C. After addition, the reaction mixture was allowed to warm to r.t. over 2 h. The reaction solvent was removed under reduced pressure. The residue was treated with water and extracted with EtOAc twice. The combined organic extracts were washed with brine, dried over Na₂SO₄ and concentrated. The crude product was purified by silica gel column chromatography (Petroleum ether→Petroleum ether:EtOAc=10:1) to afford ethyl 2-(6-chloro-2-methoxypyridin-3-yl)propanoate (126.5 g 62%) as a yellow oil. $^1$H NMR (400 MHz, CDCl$_3$) δ 1.21 (t, 3H), 1.44 (d, 3H), 3.88 (q, 1H), 3.95 (s, 3H), 4.13 (q, 2H), 6.89 (d, 1H), 7.46 (d, 1H).

Step 4: Ethyl 2-(6-chloro-2-methoxypyridin-3-yl)-3-cyano-2-methylpropanoate

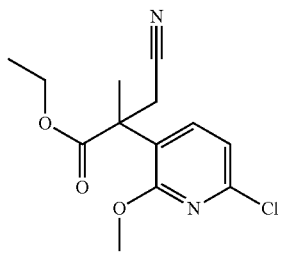 [SMILES: CCOC(=O)C(C)(CC#N)c1ccc(Cl)nc1OC]

The following reaction was repeated twice and combined to provide the yield below. To a −78° C. solution of crude ethyl 2-(6-chloro-2-methoxypyridin-3-yl)propanoate (69 g, 0.28 mol) in dry THF (1.0 L) was added lithium bis(trimethylsilyl)amide/THF (1.0 M, 400 mL, 0.40 mol) dropwise and stirred for 40 min. A solution of 2-bromoacetonitrile (54.5 g, 0.45 mol) in THF (70 mL) was then added dropwise over 1 h at −70° C. The reaction was then warmed to r.t. and stirred overnight. The reaction was quenched with saturated aqueous NH$_4$Cl and extracted with EtOAc. The organic layer was dried over Na$_2$SO$_4$ and concentrated. Purification by silica gel column chromatography (2-8% EtOAc/PE) provided ethyl 2-(6-chloro-2-methoxypyridin-3-yl)-3-cyano-2-methylpropanoate (100 g, 62%) as an oil which solidified over several days. $^1$H NMR (600 MHz, CDCl$_3$) δ 1.19 (t, 3H), 1.76 (s, 3H), 3.13 (q, 2H), 3.96 (s, 3H), 4.14-4.24 (m, 2H), 7.02 (d, 1H), 7.60 (d, 1H).

Step 5: (R)-3-(6-chloro-2-methoxypyridin-3-yl)-3-methylpyrrolidin-2-one

The following reaction was repeated twice and the combined yield is shown below. A mixture of ethyl 2-(6-chloro-2-methoxypyridin-3-yl)-3-cyano-2-methylpropanoate (47 g, 0.17 mol) and platinum oxide (6 g) in MeOH (900 mL) and concentrated hydrochloric acid (25 mL) was hydrogenated under hydrogen (50 psi) at r.t. for 48 h. The catalyst was filtered off and the filtrate was concentrated. The crude residue from the two batches were combined and used for the next reaction without any further purification.

A mixture of the crude residue above (100 g, 0.33 mmol) and potassium carbonate (70 g, 0.51 mol) in MeOH (1.6 L) was refluxed for 20 h. The solid was filtered off and washed with MeOH. The filtrate was concentrated. Purification by silica gel column chromatography (20-50% EtOAc/PE) provided 3-(6-chloro-2-methoxypyridin-3-yl)-3-methylpyrrolidin-2-one (45 g, 56%) as a solid. The racemate was separated via preparative SFC.

Peak 1: (S)-3-(6-chloro-2-methoxypyridin-3-yl)-3-methylpyrrolidin-2-one

Analytical chiral SFC retention time of 5.392 min (Method: Column: Phenomenex Lux Amylose-2, 4.6 mm×250 mm, 5 μm; Mobile Phase A: CO$_2$, Mobile Phase B: Methanol; Gradient: Hold 95% A for 1.5 min, then a linear gradient from 95% A to 40% A over 9 min, hold 40% A for 1.0 min, then equilibrate column at 95% A for 1.0 min. Flow: 3 mL/min; Backpressure 120 Bar; Column Temperature: 40° C.; UV detection 210 nm).

Preparative conditions are as follows: Column: Phenomenex Lux Amylose-2 21.2 mm×500 mm, 5 μm; Isocratic mobile phase: 80% CO$_2$:20% Methanol: Backpressure: 120 Bar; Flow: 80 mL/min, System temperature 40° C.; UV detection 210 nm.

Based on the X-ray analysis in Example 6, step 1 using peak 2 which was assigned as (R)-enantiomer, peak 1 was assigned as (S)-enantiomer.

Peak 2: (R)-3-(6-chloro-2-methoxypyridin-3-yl)-3-methylpyrrolidin-2-one

Chiral SFC retention time 5.94 min (same method as peak 1 above). Further purification by silica gel column chromatography (0-2% MeOH/DCM) provided 5.2 g of (R)-3-(6-chloro-2-methoxypyridin-3-yl)-3-methylpyrrolidin-2-one containing an impurity. The impure material (15.7 g) was further purified by preparative HPLC retention time: 2.597 min (Method: Column: Luna (2) C18 150 mm×21.2 mm, 5 μm, Mobile Phase A: 0.1% Formic Acid in Water. Mobile Phase B: 0.1% formic acid in Methanol, Flow: 27.0 mL/min, Gradient: Initial conditions: A-95%; B-5%, hold 0-1.5 min.; Ramp to B-100% from 1.5 to 10 min.; hold from 10-11 min.; return to initial conditions A-95%:B-5% from 11 to 12.5 min. $^1$H NMR (600 MHz, CDCl$_3$) δ: 1.56 (s, 3H), 2.07 (ddd, 1H), 2.58 (ddd, 1H), 3.37 (td, 1H), 3.39-3.45 (m, 1H), 3.97 (s, 3H), 5.88 (br. s., 1H), 6.89 (d, 1H), 7.61 (d, 1H); MS (ES+)(M+H) 241. Peak 2 was used to synthesize Example 6, and the absolute stereo configuration was confirmed by X-ray crystallographic analysis (Example 6, step 1).

Alternative Route: 3-(6-chloro-2-methoxypyridin-3-yl)-3-methylpyrrolidin-2-one

Step 1: methyl 2-(6-chloro-2-methoxypyridin-3-yl)propanoate

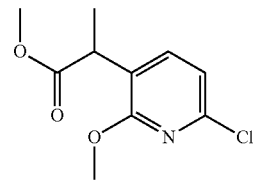

To a dry flask was added 3-bromo-6-chloro-2-methoxypyridine (9.7 g, 43.7 mmol), palladium(0)bis(dibenzylideneacetone) (1.3 g, 2.2 mmol), and zinc fluoride (3.4 g, 32.7 mmol). The mixture was degassed with nitrogen. A solution of tri-tert-butylphoshine/toluene (1.0 M, 4.4 mL, 4.4 mmol) in DMF (146 mL) was then added to the degassed mixture. After stirring, (E)-(1-methoxyprop-1-enyloxy)trimethylsilane (15.2 mL, 65 mmol) was added and the reaction was heated at 85° C. for 18 h. The mixture was partitioned between MTBE and brine. The aqueous layer was extracted with MTBE. The combined organic layers were dried over Na$_2$SO$_4$ and concentrated. Purification by silica gel column chromatography (330 g RediSep Gold column, 30-65% DCM/heptanes) provided methyl 2-(6-chloro-2-methoxypyridin-3-yl)propanoate (6.4 g, 64%); ¹H NMR (600 MHz, CDCl₃) δ: 1.44 (d, 3H), 3.67 (s, 3H), 3.91 (q, 1H), 3.95 (s, 3H), 6.89 (d, 1H), 7.45 (d, 1H).

Step 2: methyl 2-(6-chloro-2-methoxypyridin-3-yl)-3-cyano-2-methylpropanoate

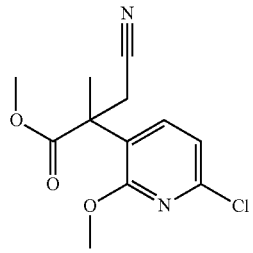 [SMILES: COC(=O)C(C)(CC#N)c1ccc(Cl)nc1OC]

In a dry flask containing lithium bis(trimethylsilyl)amide/toluene (1.0 M, 13.1 mL, 13.1 mmol) and THF (18 mL) at −78° C. was added methyl 2-(6-chloro-2-methoxypyridin-3-yl)propanoate (2.39 g, 10.4 mmol) dropwise via syringe over 12 min resulting in a bright yellow solution. After 40 min, the resulting solution was added dropwise to a dry flask containing a solution of 2-bromoacetonitrile (1.38 mL, 20.8 mmol) in THF (18 mL) at 0° C. over 15 min, resulting in a color change from colorless to yellow to dark red-brown. Subsequent rinses with THF (2×1.5 mL) were cannulated over. After 50 min, the reaction was quenched with saturated aqueous ammonium chloride (18 mL). The mixture was diluted with heptanes (4× the reaction volume). The aqueous layer was extracted 2× with 1:1 EtOAc/heptanes (200 mL). The combined organic layers were dried over Na₂SO₄ and concentrated. Purification by silica gel column chromatography (220 g RediSep Gold column, 5-18% EtOAc/heptanes) provided methyl 2-(6-chloro-2-methoxypyridin-3-yl)-3-cyano-2-methylpropanoate (2.35 g, 84%) as a white solid. ¹H NMR (600 MHz, CDCl₃) δ: 1.74 (s, 3H), 3.07 (d, 1H), 3.14 (d, 1H), 3.67 (s, 3H), 3.95 (s, 3H), 7.00 (d, 1H), 7.57 (d, 1H); MS (AP+) (M+H) 269.

Step 3: 3-(6-chloro-2-methoxypyridin-3-yl)-3-methylpyrrolidin-2-one

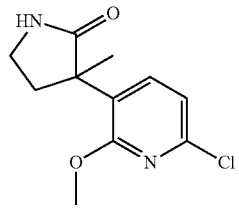 [SMILES: COc1nc(Cl)ccc1C1(C)CCNC1=O]

A Parr bottle was charged with a solution of methyl 2-(6-chloro-2-methoxypyridin-3-yl)-3-cyano-2-methylpropanoate (2.35 g, 8.73 mmol) in 7 M ammonia in MeOH and a slurry of Raney nickel (5.82 g, 67.9 mmol, washed 2× with water and 4× with MeOH) in 7 M ammonia in MeOH (99 mL total to charge both reagents, 690 mmol). The reaction was shaken with hydrogen (30 psi) for 6 h. The catalyst was filtered through a pad of Celite® under nitrogen rinsing with EtOH. The filtrate was then concentrated to give a light green oil/foam. Purification by silica gel column chromatography (80 g RediSep Gold column, 30-100% Ethyl acetate/Heptanes) provided 3-(6-chloro-2-methoxypyridin-3-yl)-3-methylpyrrolidin-2-one (1.9 g, 90%) as a white solid. ¹H NMR (600 MHz, CDCl₃) δ: 1.56 (s, 3H), 2.08 (ddd, 1H), 2.58 (dt, 1H), 3.37 (td, 1H), 3.40-3.46 (m, 1H), 3.97 (s, 3H), 5.86 (br. s., 1H), 6.89 (d, 1H), 7.61 (d, 1H); MS (ES+)(M+H) 241.

6-Bromo-1-ethyl-4-fluoro-1H-indazole

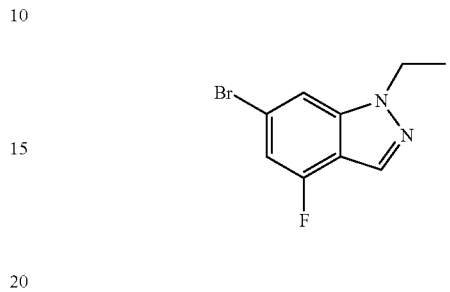

Step 1: 6-Bromo-4-fluoro-1H-indazole

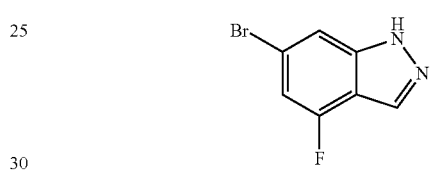

A mixture of 4-bromo-2,6-difluorobenzaldehyde (50 g, 226 mmol) and N₂H₄—H₂O (100 mL) in 1,4-dioxane (100 mL) was heated to 95° C. and stirred at this temperature for 1.5 h. After being cooled to r.t., the reaction mixture was poured into ice water and extracted with EtOAc. The organic layer was dried and concentrated to give 6-bromo-4-fluoro-1H-indazole (35 g, 163 mmol, 71%) as a yellow solid, which was used for the next step without any further purification.

Step 2: 6-Bromo-1-ethyl-4-fluoro-1H-indazole

To a solution of 6-bromo-4-fluoro-1H-indazole (1000 g, 4.65 mol) in DMSO (5.0 L), was added K₂CO₃ (900 g, 6.51 mol), followed by addition of ethyl iodide (900 g, 5.77 mol). The reaction mixture was stirred at r.t. for 16 h. The reaction mixture was poured into ice water and extracted with EtOAc. The organic layer was dried and concentrated. The residue was purified by silica gel column chromatography (0-10% EtOAc in hexanes) to give 6-bromo-1-ethyl-4-fluoro-1H-indazole (595 g, 2.45 mol, 52%) as a yellow oil and 6-bromo-2-ethyl-4-fluoro-2H-indazole (278 g, 1.14 mol, yield 17%) as an orange solid. ¹H NMR (600 MHz, CDCl₃) δ 1.52 (t, 3H), 4.39 (q, 2H), 6.95 (dd, 1H), 7.40 (s, 1H), 8.02 (s, 1H). MS (ES+)(M+H) 243.

Alternative Synthesis of 6-Bromo-1-ethyl-4-fluoro-1H-indazole

To a solution of 4-bromo-2,6-difluorobenzaldehyde (1000 mg, 4.5 mmol) in NMP (10 mL) was added ethyl hydrazine oxalate (747 mg, 5.0 mmol). The reaction mixture was stirred at r.t. for 72 h. The reaction mixture was heated under reflux for 15 h. After being cooled at r.t., the reaction mixture was partitioned between heptane and water. The aqueous layer was extracted with heptane. The combined organic extracts were washed with brine, dried over MgSO₄, and concentrated under reduced pressure. The crude product was purified by silica gel column chromatography (0-20% EtOAc in heptanes) to afford 6-bromo-1-ethyl-4-fluoro-1H-indazole as a light yellow oil (902 mg, 84%).

6-Bromo-4-chloro-1-methyl-1H-indazole

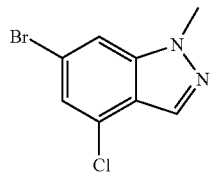

To a mixture of 6-bromo-4-chloro-1H-indazole (4.0 g, 17.4 mmol), cesium hydroxide monohydrate (23.3 g, 139 mmol), tetrabutylammonium hydrogensulfate (1.36 g, 3.99 mmol) in anhydrous THF (80 mL) was added a solution of methyl iodide (9.86 g, 69.4 mmol) in THF (10 mL) dropwise at r.t. The reaction mixture was stirred for 15 min at r.t. Water was added to the reaction mixture, and the aqueous layer was extracted with EtOAc. The organic layer was concentrated, and the crude reside was purified by silica gel column chromatography (EtOAc/Heptane 0 to 100% gradient as eluent) to afford 6-Bromo-4-chloro-1-methyl-1H-indazole (2.65 g, 62%). $^1$H NMR (600 MHz, methanol-$d_4$) δ 4.05 (s, 3H), 7.32 (d, 1H), 7.79 (s, 1H), 8.03 (s, 1H).

6-Bromo-1-ethyl-4-methyl-1H-indazole

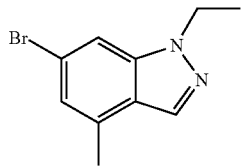

To a solution of 6-bromo-4-methyl-1H-indazole (1000 mg, 4.7 mmol) in THF (15 mL) was added sodium hydroxide (474 mg, 11.8 mmol) and tetrabutylammonium hydrogen sulfate (80.5 mg, 0.24 mmol). The reaction mixture was stirred at r.t. for 1 h and then treated with ethyl iodide (887 mg, 5.7 mmol) dropwise. The resulting mixture was stirred at r.t. overnight. The mixture was concentrated under reduced pressure and the residue was purified by silica gel column chromatography (0-100% EtOAc in heptane) to afford 6-Bromo-1-ethyl-4-methyl-1H-indazole (476 mg, 42%). $^1$H NMR (600 MHz, CDCl$_3$) δ 1.51 (t, 3H), 2.57 (s, 3H), 4.38 (q, 2H), 7.04-7.06 (m, 1H), 7.43 (s, 1H), 7.97 (d, 1H). MS (AP+)(M+H) 239.

Example 1

(R)-6-(1-ethyl-4-fluoro-1H-indazol-6-yl)-3-(3-methyl-2-oxopiperidin-3-yl)pyridin-2(1H)-one; Tautomer (R)-3-(6-(1-ethyl-4-fluoro-1H-indazol-6-yl)-2-hydroxypyridin-3-yl)-3-methylpiperidin-2-one

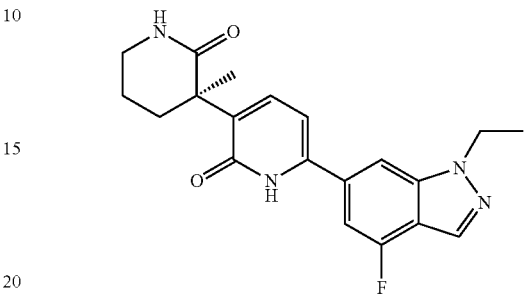

Step 1: (R)-3-(6-(1-ethyl-4-fluoro-1H-indazol-6-yl)-2-methoxypyridin-3-yl)-3-methylpiperidin-2-one

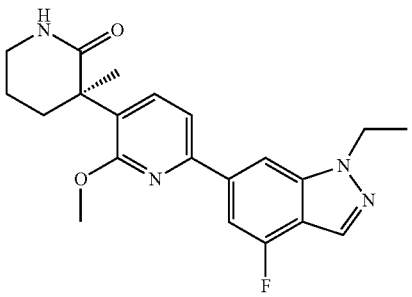 [SMILES: CCn1ncc2c(F)cc(-c3ccc([C@@]4(C)CCCNC4=O)c(OC)n3)cc21]

An oven dried vial was charged with 6-bromo-1-ethyl-4-fluoro-1H-indazole (900 mg, 3.7 mmol), 5,5,5',5'-tetramethyl-2,2'-bi(1,3,2-dioxaborinane) (1000 mg, 4.4 mmol), oven dried KOAc (1450 mg, 14.8 mmol), anhydrous dioxane (5 mL) and [1,1'-Bis(diphenylphosphino)ferrocene]dichloropalladium(II) complex with dichloromethane (75.9 mg, 0.093 mmol). The mixture was purged with nitrogen gas for 5 min. The reaction vial was sealed and heated at 110° C. for 1.5 h. After being cooled to r.t., to the reaction mixture was added (R)-3-(6-chloro-2-methoxypyridin-3-yl)-3-methylpiperidin-2-one (943 mg, 3.7 mmol), an aqueous solution of sodium carbonate (2 M, 4.6 mL, 9.3 mmol) and an additional [1,1'-Bis(diphenylphosphino)-ferrocene]-dichloropalladium(II) complex with dichloromethane (75.9 mg, 0.093 mmol). The reaction mixture was degassed with nitrogen, and heated at 100° C. for 3 h. The reaction mixture was cooled to r.t., diluted with EtOAc, and the organic layer was washed with brine and water, dried over MgSO$_4$, and concentrated under reduced pressure. The crude residue was purified by silica gel column chromatography (0-20% EtOH/DCM) to afford (R)-3-(6-(1-ethyl-4-fluoro-1H-indazol-6-yl)-2-methoxypyridin-3-yl)-3-methylpiperidin-2-one (1140 mg, 81%). $^1$H NMR (600 MHz, CDCl$_3$) δ 1.57 (t, 3H), 1.67-1.71 (m, 1H), 1.74 (s, 3H), 1.84 (d, 1H), 1.97-2.07 (m, 1H), 2.35-2.44 (m, 1H), 3.44 (br. s., 1H), 3.55 (br. s., 1H), 4.12 (s, 3H), 4.50 (q, 2H), 5.92 (br. s., 1H), 7.41 (d, 1H), 7.48 (d, 1H), 7.69 (d, 1H), 7.84 (s, 1H), 8.06 (s, 1H). MS (AP+)(M+H) 383.

Step 2

To a solution of (R)-3-(6-(1-ethyl-4-fluoro-1H-indazol-6-yl)-2-methoxypyridin-3-yl)-3-methylpiperidin-2-one (1140 mg, 2.98 mmol) in acetonitrile (20 mL) was added sodium iodide (894 mg, 5.96 mmol), followed by dropwise addition of TMSCI (760 uL, 5.96 mmol) at 0° C. The reaction mixture was allowed to warm up to r.t. and stirred for 20 h. The reaction was quenched by addition of 0.5 M aqueous solution of sodium thiosulfate (about 30 mL), and the resulting mixture was stirred at r.t. for 30 min. The mixture was diluted with water and the aqueous layer was extracted with DCM 3 times.

The combined organic extracts were washed with brine, dried over MgSO$_4$ and concentrated under reduced pressure. The crude product was purified by silica gel column chromatography (0-25% EtOH in DCM) to afford Example 1 (803 mg, 73%) as an off-white powder. $^1$H NMR (600 MHz, methanol-d$_4$) δ 1.52 (t, 3H), 1.57 (dd, 1H), 1.63 (s, 3H), 1.82-1.85 (m, 1H), 2.00-2.07 (m, 1H), 2.41 (td, 1H), 3.33-3.36 (m, 1H), 3.53 (td, 1H), 4.54 (q, 2H), 6.73 (d, 1H), 7.17 (d, 1H), 7.64 (d, 1H), 7.77 (s, 1H), 8.13 (s, 1H). MS (ES+)(M+H) 369.

Alternatively, Example 1 is prepared as follows. A round bottom flask was charged with (R)-3-(6-chloro-2-methoxypyridin-3-yl)-3-methylpiperidin-2-one (48 g, 189 mmol), palladium XPhos (generation II precatalyst) (2.97 g, 3.8 mmol, 2 mol %), and 6-(5,5-dimethyl-1,3,2-dioxaborinan-2-yl)-1-ethyl-4-fluoro-1H-indazole (66.6 g, 210 mmol, 1.1 equiv). The flask was evacuated and backfilled with nitrogen three times. Nitrogen gas-sparged tetrahydrofuran (500 mL) was then added, followed by the addition of aqueous 2M sodium carbonate (236 mL, 472 mmol, 2.50 equiv). The mixture was heated at 60° C. for 90 minutes, cooled to r.t., then diluted with water (250 mL) and ethyl acetate (250 mL). The mixture was extracted with ethyl acetate (3×250 mL), and the combined organics were dried over sodium sulfate and filtered. Concentration of the filtrate afforded a brown solid, which was dissolved in dichloromethane (250 mL). Thiol-capped Silica Gel (Silacycle) (55 g, loading=4.28 mmol/g) was added, and the suspension was stirred for 30 min before filtering through a short pad of Celite® over a short pad of silica gel. The filter cake was rinsed with 5% ethanol:dichloromethane (3×50 mL), and the filtrate was concentrated to dryness to afford a light brown solid. This material was suspended in ethyl acetate (200 mL) at 50° C. for 1 h then stirred at r.t. for 72 h. The solids were collected by filtration and drying under vacuum to afford an off-white powder (62.5 g, 86%). This material was carried into the next step without further purification.

To a suspension of (R)-3-(6-(1-ethyl-4-fluoro-1H-indazol-6-yl)-2-methoxypyridin-3-yl)-3-methylpiperidin-2-one (62.0 g, 160 mmol) in acetonitrile (3.2 L) at r.t. was added sodium iodide (72.9 g, 486 mmol, 3 equiv), followed by the dropwise addition of chlorotrimethylsilane (171 mL, 486 mmol, 3.0 equiv) over 15 min. The resulting light purple suspension was stirred at r.t. for 16 h then heated at 40° C. for another 16 h to drive completion. The mixture was allowed to reach r.t. then filtered over a pad of Celite® and concentrated to afford a reddish brown solid. This residue was dissolved in dichloromethane (200 mL) and washed with water (2×200 mL). The organic layer was dried over sodium sulfate, filtered, and concentrated to afford a brown solid, which was suspended in methyl tert-butylether (275 mL) and stirred at 40° C. for another 16 h. The suspension was then filtered, rinsed with additional methyl tert-butylether, and dried under vacuum to afford Example 1 as a light tan solid (57.2 g, 96%).

Example 2

(R)-6-(4-chloro-1-methyl-1H-indazol-6-yl)-3-(3-methyl-2-oxopiperidin-3-yl)pyridin-2(1H)-one; Tautomer (R)-3-(6-(4-chloro-1-methyl-1H-indazol-6-yl)-2-hydroxypyridin-3-yl)-3-methylpiperidin-2-one

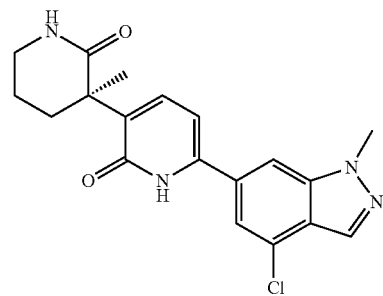

Step 1: (R)-3-(6-(4-chloro-1-methyl-H-indazol-6-yl)-2-methoxypyridin-3-yl)-3-methylpiperidin-2-one

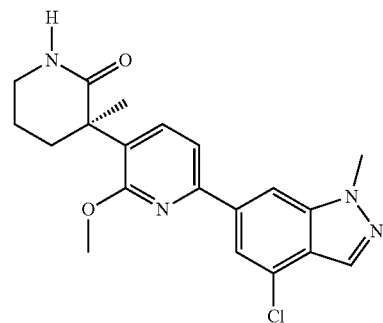 [SMILES: COc1nc(-c2cc(Cl)c3cnn(C)c3c2)ccc1[C@@]1(C)CCCNC1=O]

An oven dried vial was charged with 6-bromo-4-chloro-1-methyl-1H-indazole (507 mg, 2.1 mmol), 5,5,5',5'-tetramethyl-2,2'-bi(1,3,2-dioxaborinane) (649 mg, 1.9 mmol), oven dried KOAc (604 mg, 6.2 mmol), [1,1'-Bis(diphenylphosphino)-ferrocene]dichloropalladium(II) complex with dichloromethane (54 mg, 0.066 mmol) and dioxane (10 mL), and purged with nitrogen for 20 min. The reaction was heated at 100° C. for 1 h. The mixture was filtered through a pad of Celite®, and the filter cake was rinsed with dioxane. The filtrate was concentrated under reduced pressure to afford the crude residue (530 mg). To a solution of this crude residue (370 mg) in degassed dioxane (2 mL) was added (R)-3-(6-chloro-2-methoxypyridin-3-yl)-3-methylpiperidin-2-one (300 mg, 1.2 mmol), an aqueous solution of sodium carbonate (2 M, 1.5 mL, 2.9 mmol) and [1,1'-Bis(diphenylphosphino)ferrocene]dichloropalladium(II) complex with dichloromethane (54 mg, 0.066 mmol). The reaction mixture was degassed with nitrogen, and heated at 100° C. for 1 h. The reaction mixture was cooled to r.t., and anhydrous Na$_2$SO$_4$ was added. The mixture was filtered through a pad of Celite®, and the filter cake was rinsed with dioxane. The filtrate was concentrated under reduced pressure. The crude product was purified by silica gel column chromatography (0-100%

EtOAc in Heptane to 0-30% EtOH/DCM) to afford (R)-3-(6-(4-chloro-1-methyl-1H-indazol-6-yl)-2-methoxypyridin-3-yl)-3-methylpiperidin-2-one (358 mg, 79%). ¹H NMR (600 MHz, CDCl₃) δ 1.68 (d, 1H), 1.74 (s, 3H), 1.88 (d, 1H), 1.97-2.07 (m, 1H), 2.39 (td, 1H), 3.37-3.47 (m, 1H), 3.50-3.60 (m, 1H), 4.12 (s, 3H), 4.15 (s, 3H), 5.81 (brs, 1H), 7.42 (d, 1H), 7.70 (d, 1H), 7.82 (s, 1H), 7.94 (s, 1H), 8.06 (s, 1H). MS (AP+)(M+H) 385.

Step 2

To a solution of (R)-3-(6-(4-chloro-1-methyl-1H-indazol-6-yl)-2-methoxypyridin-3-yl)-3-methylpiperidin-2-one (51 mg, 0.13 mmol) in acetonitrile (0.5 mL) was added a 46% aqueous HBr (0.5 mL), and the reaction mixture was heated at 90° C. for 15 min. The reaction mixture was partitioned into DCM and water, and the aqueous layer was extracted with DCM. The combined organic extracts were concentrated under reduced pressure. The crude residue was triturated in acetonitrile (1 mL), followed by filtration of the resulting solid to afford Example 2 (41 mg, 84%). ¹H NMR (600 MHz, methanol-d₄) δ 1.62-1.70 (m, 1H), 1.66 (s, 3H), 1.84-1.92 (m, 1H), 2.00-2.10 (m, 1H), 2.41 (td, 1H), 3.37-3.44 (m, 1H), 3.53 (td, 1H), 4.15 (s, 3H), 6.82 (dd, 1H), 7.50 (d, 1H), 7.73 (dd, 1H), 7.89 (s, 1H), 8.11 (s, 1H). MS (ES+)(M+H) 371.

Example 3

(R)-6-(1-ethyl-4-methyl-1H-indazol-6-yl)-3-(3-methyl-2-oxopiperidin-3-yl)pyridin-2(1H)-one; Tautomer (R)-3-(6-(1-ethyl-4-methyl-1H-indazol-6-yl)-2-hydroxypyridin-3-yl)-3-methylpiperidin-2-one

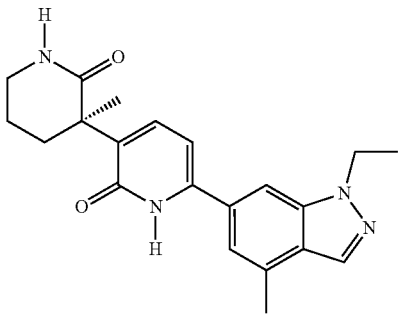 [SMILES: CCn1ncc2c(C)cc(-c3ccc([C@@]4(C)CCCNC4=O)c(=O)[nH]3)cc21]

Step 1: (R)-3-(6-(1-ethyl-4-methyl-1H-indazol-6-yl)-2-methoxypyridin-3-yl)-3-methylpiperidin-2-one

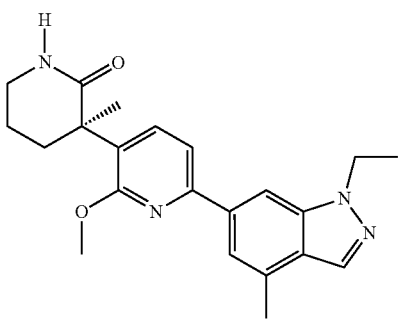 [SMILES: CCn1ncc2c(C)cc(-c3ccc([C@@]4(C)CCCNC4=O)c(OC)n3)cc21]

An oven-dried 20 mL vial was charged with 6-bromo-1-ethyl-4-methyl-1H-indazole (345 mg, 1.4 mmol), 5,5,5',5'-tetramethyl-2,2'-bi(1,3,2-dioxaborinane) (591 mg, 1.7 mmol), oven dried KOAc (566 mg, 5.8 mmol), anhydrous dioxane (5 mL) and [1,1'-Bis(diphenylphosphino)ferrocene]dichloropaladium(II) complex with dichloromethane (56.8 mg, 0.072 mmol). The mixture was bubbled with nitrogen gas for 5 minutes, and the reaction vial was sealed and heated at 110° C. for 1 h. After being cooled to r.t., to the reaction mixture was added (R)-3-(6-chloro-2-methoxypyridin-3-yl)-3-methylpiperidin-2-one (294 mg, 1.2 mmol), an aqueous solution of sodium carbonate (2M, 1.8 mL, 3.6 mmol) and additional [1,1'-Bis(diphenylphosphino)-ferrocene]dichloropalladium(II) complex with dichloromethane (56.8 mg, 0.072 mmol). The reaction mixture was degassed with nitrogen, and heated at 100° C. for 75 min. The reaction mixture was cooled to r.t., diluted with EtOAc, filtered over Celite®, and the filtrate was concentrated. The crude residue was purified by silica gel column chromatography (0-10% EtOH/DCM, 40 g column) to afford (R)-3-(6-(1-ethyl-4-methyl-1H-indazol-6-yl)-2-methoxypyridin-3-yl)-3-methylpiperidin-2-one (429 mg, 79%) as an off-white solid. ¹H NMR (600 MHz, CDCl₃) δ 1.56 (t, 3H), 1.64-1.91 (m, 2H), 1.74 (s, 3H), 1.97-2.08 (m, 1H), 2.35-2.44 (m, 1H), 2.66 (s, 3H), 3.39-3.50 (m, 1H), 3.51-3.62 (m, 1H), 4.13 (s, 3H), 4.51 (q, 2H), 6.07 (brs, 1H), 7.43 (d, 1H), 7.55 (s, 1H), 7.68 (d, 1H), 7.89 (s, 1H), 8.01 (s, 1H). MS (AP+)(M+H) 379.

Step 2

To a solution of (R)-3-(6-(1-ethyl-4-methyl-1H-indazol-6-yl)-2-methoxypyridin-3-yl)-3-methylpiperidin-2-one (420 mg, 1.1 mmol) in DMF (5 mL) was added sodium n-propane thiolate (1090 mg, 11.1 mmol). The vial was sealed and the reaction was heated at 110° C. for 1 h. The reaction was allowed to be cooled to r.t. overnight. The reaction mixture was concentrated under reduced pressure, and the residue was partitioned between 15% EtOH/DCM and pH 7 phosphate buffer. The aqueous layer was extracted with 15% EtOH/DCM (2×50 mL). The combined organic extracts were washed with brine, dried over MgSO₄, and concentrated under reduced pressure. The crude residue was purified by means of MPLC (0-20% EtOH/DCM, 40 gram ISCO column) to obtain Example 3 (230 mg, 57%) as a white powder. ¹H NMR (600 MHz, methanol-d₄) δ 1.50 (t 3H), 1.56-1.59 (m, 1H), 1.63 (s, 3H), 1.82-1.85 (m, 1H), 2.01-2.05 (m, 1H), 2.42 (td, 1H), 2.66 (s, 3H), 3.33-3.36 (m, 1H), 3.54 (td, 1H), 4.52 (q, 2H), 6.71 (d, 1H), 7.23 (s, 1H), 7.64 (d, 1H), 7.72 (s, 1H), 8.11 (s, 1H). MS (ES+)(M+H) 365.

Example 4

(R)-6-(1-methyl-1H-indol-6-yl)-3-(3-methyl-2-oxopiperidin-3-yl)pyridin-2(1H)-one; Tautomer (R)-3-(2-hydroxy-6-(1-methyl-1H-indol-6-yl)pyridin-3-yl)-3-methylpiperidin-2-one

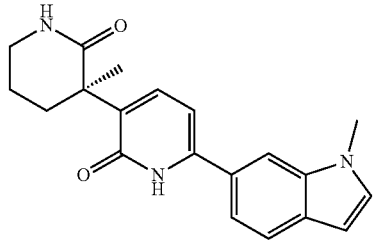 [SMILES: Cn1ccc2ccc(-c3ccc([C@@]4(C)CCCNC4=O)c(=O)[nH]3)cc21]

Step 1: (R)-3-(2-methoxy-6-(1-methyl-1H-indol-6-yl)pyridin-3-yl)-3-methylpiperidin-2-one

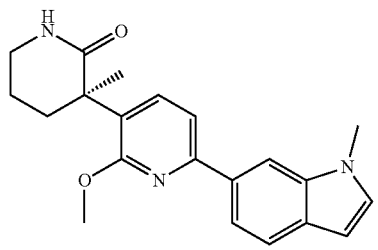 [SMILES: COc1nc(-c2ccc3ccn(C)c3c2)ccc1[C@@]1(C)CCCNC1=O]

To a vessel containing (R)-3-(6-chloro-2-methoxypyridin-3-yl)-3-methylpiperidin-2-one (80 mg, 0.31 mmol), 1-methyl-6-(4,4,5,5-tetramethyl-1,3,2-dioxaborolan-2-yl)-1H-indole (105 mg, 0.41 mmol), dioxane (3 mL), and 2 M $Na_2CO_3$ (0.31 mL, 0.63 mmol) was added Pd(dppf)$Cl_2$ (23 mg, 0.031 mmol). The reaction was stirred for 18 h at 110° C. The mixture was diluted with ethyl acetate (50 mL) and washed with brine (15 mL). The organic layer was dried over $Na_2SO_4$, filtered, and concentrated to provide a crude product. Purification by preparative TLC (100% Ethyl Acetate) provided the title compound (80 mg, 76%). $^1$H NMR (400 MHz, $CDCl_3$) δ: 1.65-1.70 (m, 1H); 1.72 (s, 3H), 1.78-1.84 (m, 1H), 1.95-2.05 (m, 1H), 2.40 (td, 1H), 3.35-3.41 (m, 1H), 3.52 (td, 1H), 3.87 (s, 3H), 4.11 (s, 3H), 5.83 (br. s., 1H), 6.49 (d, 1H), 7.10 (d, 1H), 7.41 (d, 1H), 7.64-7.67 (m, 2H), 7.77 (dd, 1H), 8.03 (s, 1H).

Step 2

To a vessel containing (R)-3-(2-methoxy-6-(1-methyl-1H-indol-6-yl)pyridin-3-yl)-3-methylpiperidin-2-one (70 mg, 0.21 mmol) in DMF (4 mL) was added sodium 1-propanethiolate (410 mg, 4.2 mmol) at r.t. The reaction was stirred for 16 h at 110° C. The mixture was filtered and sent for HPLC purification (HPLC retention time: 10.0 min (Method: Column: Agela Durashell C18 250×21.2 mm, 8 μm, Mobile Phase A: 0.225% Formic Acid in Water, Mobile Phase B: acetonitrile, Flow: 30.0 mL/min, Gradient: Initial conditions: Ramp A-79%:B-21% over 11 min.; A-0%:B-100% hold from 11-13 min; Detection 220 nm). The solution was lyophilized to provide Example 4 (30 mg, 43%) as a yellow solid. $^1$H NMR (400 MHz, methanol-$d_4$) δ: 1.53-1.61 (m, 1H), 1.62 (s, 3H), 1.78-1.88 (m, 1H), 1.98-2.06 (m, 1H), 2.43 (td, 1H), 3.34-3.38 (m, 1H), 3.53 (td, 1H), 3.88 (s, 3H), 6.49 (d, 1H), 6.68 (d, 1H), 7.29 (d, 1H), 7.34 (dd, 1H), 7.60-7.68 (m, 2H), 7.73 (s, 1H); MS (ES+)(M+H) 336.

Example 5

(R)-6-(1-methyl-1H-indol-5-yl)-3-(3-methyl-2-oxopiperidin-3-yl)pyridin-2(1H)-one; Tautomer (R)-3-(2-hydroxy-6-(1-methyl-1H-indol-5-yl)pyridin-3-yl)-3-methylpiperidin-2-one

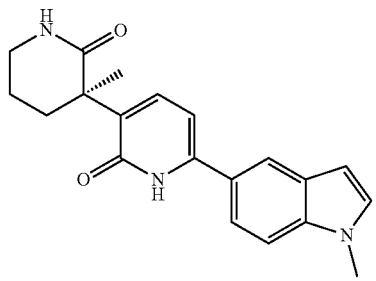 [SMILES: Cn1ccc2cc(-c3ccc([C@@]4(C)CCCNC4=O)c(=O)[nH]3)ccc21]

Step 1: (R)-3-(2-methoxy-6-(1-methyl-1H-indol-5-yl)pyridin-3-yl)-3-methylpiperidin-2-one

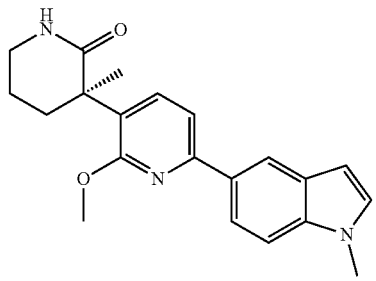 [SMILES: COc1nc(-c2ccc3c(ccn3C)c2)ccc1[C@@]1(C)CCCNC1=O]

To a large microwave vial was added (R)-3-(6-chloro-2-methoxypyridin-3-yl)-3-methylpiperidin-2-one (1.20 g, 4.7 mmol), 1-methyl-1H-indol-5-ylboronic acid (0.82 g, 4.7 mmol), dioxane (10 mL), 2 M $Na_2CO_3$ (5.9 mL, 11.8 mmol), and $PdCl_2$(dppf) $CH_2Cl_2$ (193 mg, 0.236 mmol). Nitrogen gas was bubbled through the reaction mixture for 5 minutes prior to sealing the vessel. The reaction was stirred for 18 h at 105° C. The mixture was cooled to r.t., diluted with ethyl acetate, and filtered over Celite®. The filtrate was concentrated to a brown paste. Purification by column chromatography (80 g RediSep Gold column) with a 0-10% EtOH/DCM gradient provided (R)-3-(2-methoxy-6-(1-methyl-1H-indol-5-yl)pyridin-3-yl)-3-methylpiperidin-2-one (1.54 g, 94%) as a light orange solid. $^1$H NMR (600 MHz, $CDCl_3$) δ: 1.62-1.69 (m, 1H), 1.72 (s, 3H), 1.77-1.86 (m, 1H), 1.93-2.03 (m, 1H), 2.39 (td, 1H), 3.36-3.44 (m, 1H), 3.52 (td, 1H), 3.82 (s, 3H), 4.11 (s, 3H), 6.16 (br s., 1H), 6.56 (d, 1H), 7.07 (d, 1H), 7.36 (d, 1H), 7.38 (d, 1H), 7.62 (d, 1H), 7.93 (dd, 1H), 8.29 (s, 1H); MS (ES+)(M+H) 350.

Step 2

To a flask was added (R)-3-(2-methoxy-6-(1-methyl-1H-indol-5-yl)pyridin-3-yl)-3-methylpiperidin-2-one (1.37 g, 3.9 mmol), DMF (30 mL) and sodium n-propanethiolate (4.41 g, 39.3 mmol). The mixture was stirred for 15 h at 115° C. The mixture was cooled to r.t. and concentrated to provide a brown paste that was then partitioned between 15% EtOH/

DCM and aqueous pH 7 buffer. The aqueous phase was extracted twice and the combined organic layers were washed with brine and dried over MgSO₄ to provide a crude product. Purification by column chromatography (80 g RediSep Gold column) with a 0-25% EtOH/DCM gradient provided Example 5 (632 mg, 48%) as a white solid. ¹H NMR (400 MHz, methanol-d₄) δ: 1.53-1.60 (m, 1H), 1.62 (s, 3H), 1.78-1.87 (m, 1H), 1.94-2.08 (m, 1H), 2.42 (td, 1H), 3.34-3.37 (m, 1H), 3.53 (td, 1H), 3.85 (s, 3H), 6.55 (dd, 1H), 6.62 (d, 1H), 7.25 (d, 1H), 7.46 (dd, 1H), 7.50 (d, 1H), 7.61 (d, 1H), 7.85-7.91 (m, 1H); MS (ES+)(M+H) 336.

Alternatively, Example 5 is prepared as follows. A round bottom flask was charged with (R)-3-(6-chloro-2-methoxypyridin-3-yl)-3-methylpiperidin-2-one (60.0 g, 240 mmol) and 1-methyl-1H-indol-5-ylboronic acid (47.7 g, 259 mmol, 1.1 equiv). The flask was evacuated and backfilled with nitrogen. To the reaction vessel were then added dioxane (700 mL) and aqueous 2M sodium carbonate (295 mL, 590 mmol, 2.50 equiv). The mixture was sparged with nitrogen gas for 60 min before adding the catalyst, palladium dichloride dipphenylphosphinoferrocene dichloromethane adduct (PdCl₂dppf-CH₂Cl₂) (5.77 g, 7.07 mmol, 3 mol %). The mixture was heated to an internal temperature of 90° C. for 60 minutes, then cooled to r.t. and diluted with ethyl acetate (500 mL). The mixture was filtered through a short pad of Celite® and silica, and the filter cake was rinsed with ethyl acetate (1 L) until the filtrate was colorless. The solvent was removed and replaced with dichloromethane, which was washed with aqueous 1N sodium hydroxide (2×800 mL) then with brine (1×500 mL). The combined organics were dried over sodium sulfate and filtered. Concentration of the filtrate afforded the crude product as a tan foam. Ethyl acetate (400 mL) was added, and the mixture was heated at 80° C. for 1 h then cooled to r.t. to afford a suspension. After stirring another 3 h, the mixture was filtered, and the solids collected were dried under vacuum to afford an off-white solid, which was then suspended in acetonitrile and heated at 90° C. for 1 h then stirred at r.t. for 16 h. The solids were collected by filtration then suspended in methyl tert-butylether (400 mL). Dichloromethane (900 mL) was added to obtain a clear homogenous solution. The volume of the combined solvent was reduce by about 50% to afford a thick suspension which was left to stir as a slurry for 60 min. Filtration and drying the solids under vacuum then afforded an off-white powder (59.3 g, 72%). This material was carried into the next step without further purification.

To a solution of (R)-3-(2-methoxy-6-(1-methyl-H-indol-5-yl)pyridin-3-yl)-3-methylpiperidin-2-one (59.7 g, 171 mmol) in dimethylformamide (520 mL) was added ethyl sodium thiolate (116.6 g, 1386 mmol, 8.11 equiv). The flask was fitted with a reflux condenser topped with an outlet hose leading to an inline bubbler, which contained a thiol scrubbing solution consisting of 1:1 bleach:sodium bicarbonate (to capture volatile thiol). The reaction mixture was heated at 110° C. for 14 h then cooled to r.t. The condenser was removed and high vacuum was applied to the flask using a rotary evaporator. The dimethylformamide was removed in vacuo and water (250 mL) was added to afford a thick suspension. Phosphoric acid (2.25 M, 76 mL) was added to adjust the pH to about 6. The suspended solids were collected by filtration and dried under vacuum to afford a tan solid. This residue was triturated with acetonitrile (200 mL) and the mixture was heated to reflux for 3 h then allowed to cool to r.t. and to stir for 15 h. The solids were collected by filtration. The residue was suspended in 10:1 dichloromethane:ethanol (3.4 L) at r.t., and the mixture was filtered through a pad of Celite®. The filter cake was rinsed with 440 mL of additional solvent, and the filtrate was concentrated to dryness to afford a light tan solid. Finally, the material was suspended in 2-propanol (250 mL) and heated at 50° C. for 15 h. The suspension was filtered, and the solids were collected and dried under vacuum to afford Example 5 product as an off-white powder (56.17 g, 98%).

Example 6

(R)-6-(1-methyl-1H-indol-5-yl)-3-(3-methyl-2-oxopyrrolidin-3-yl)pyridin-2(1H)-one; Tautomer (R)-3-(2-hydroxy-6-(1-methyl-1H-indol-5-yl)pyridin-3-yl)-3-methylpyrrolidin-2-one

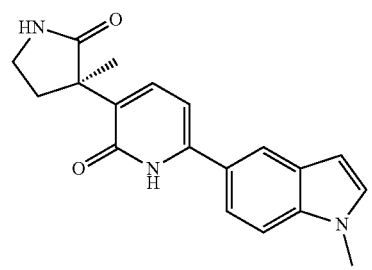 [SMILES: Cn1ccc2cc(-c3ccc([C@@]4(C)CCNC4=O)c(=O)[nH]3)ccc21]

Step 1: (R)-3-(2-methoxy-6-(1-methyl-1H-indol-5-yl)pyridin-3-yl)-3-methylpyrrolidin-2-one

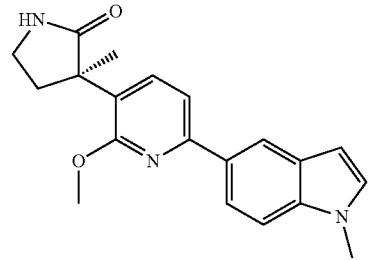 [SMILES: COc1nc(-c2ccc3c(ccn3C)c2)ccc1[C@@]1(C)CCNC1=O]

Figure 2:
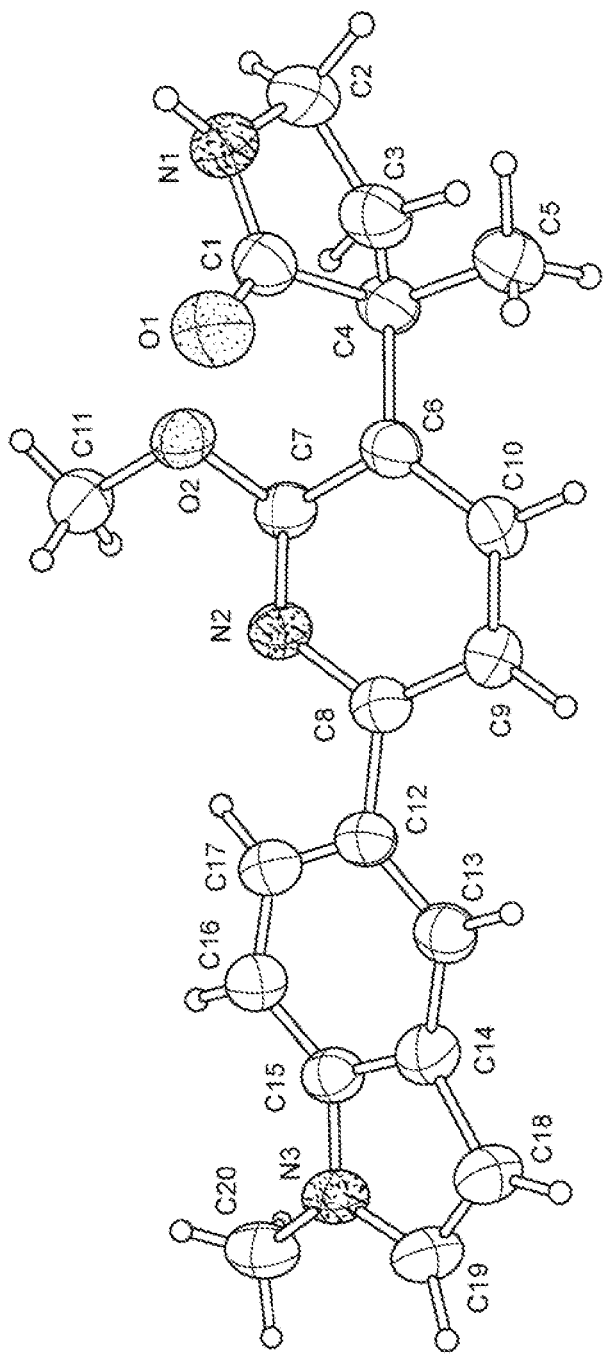
FIG. 2 is a X-ray crystal structure (ORTEP drawing) of (R)-3-(2-methoxy-6-(1-methyl-1H-indol-5-yl)pyridin-3-yl)-3-methylpyrrolidin-2-one.

To a vial was added (R)-3-(6-chloro-2-methoxypyridin-3-yl)-3-methylpyrrolidin-2-one (56.6 mg, 0.24 mmol) which was evaporated with dioxane (2.0 mL). 1-methyl-1H-indol-5-ylboronic acid (63.4 mg, 0.36 mmol) was next added followed by Pd(dppf)Cl₂ (7.5 mg, 0.01 mmol). The mixture was sealed and degassed with nitrogen. Degassed dioxane (1.9 mL) and degassed 2 M Na₂CO₃ (0.27 mL, 2.3 equiv) were then added to the solid mixture. The reaction was stirred for 16 h at 110° C. The reaction was concentrated and partitioned between EtOAc/10% (w/v) aq. Na₂CO₃. The organic layer was washed with brine, dried over Na₂SO₄, and concentrated to provide a crude brown glass. Purification by column chromatography (4 g RediSep Gold column) with a 40-100% EtOAc/heptane gradient provided the title compound (78 mg, 99%) as a pale yellow glass. ¹H NMR (600 MHz, CDCl₃) δ: 1.62 (s, 3H), 2.10 (ddd, 1H), 2.67-2.76 (m, 1H), 3.37-3.47 (m, 2H), 3.82 (s, 3H), 4.10-4.12 (m, 3H), 5.59 (br. s., 1H), 6.56 (d, 1H), 7.07 (d, 1H), 7.34-7.39 (m, 2H), 7.67 (d, 1H), 7.92-7.96 (m, 1H), 8.30 (s, 1H); MS (AP+)(M+H) 336. The absolute stereochemistry was obtained via X-ray crystallographic analysis of single crystals obtained via crystallization from a mixture of DCM and EtOH. FIG. 2 is an ORTEP drawing of (R)-3-(2-methoxy-6-(1-methyl-H-indol-5-yl)pyridin-3-yl)-3-methylpyrrolidin-2-one.

Single Crystal X-Ray Analysis for (R)-3-(2-methoxy-6-(1-methyl-1H-indol-5-yl)pyridin-3-yl)-3-methylpyrrolidin-2-one Data collection was performed on a Bruker APEX diffractometer at r.t.

The structure was solved by direct methods using SHELX software suite in the space group P2₁2₁2₁. The structure was subsequently refined by the full-matrix least squares method. The hydrogen atoms located on nitrogen were found from the Fourier difference map and refined with distances restrained. The remaining hydrogen atoms were placed in calculated positions and were allowed to ride on their carrier atoms. The final refinement included isotropic displacement parameters for all hydrogen atoms.

The analysis of the absolute structure using likelihood methods (R. W. W. Hooft et al. *J. Appl. Cryst.* (2008), 41, 96-103) was performed using PLATON (A. L. Spek, *J. Appl. Cryst.* (2003), 36, 7-13.). The final R-index was 3.1%. A final difference Fourier revealed no missing or misplaced electron density. Pertinent crystal, data collection and refinement of (R)-3-(2-methoxy-6-(1-methyl-1H-indol-5-yl)pyridin-3-yl)-3-methylpyrrolidin-2-one are summarized in Table 2, and graphically presented in FIG. 2.

TABLE 2

| Crystal data and structure refinement for Empirical formula C20 H21 N3 O2 | |
|---|---|
| Formula weight | 335.40 |
| Temperature | 298(2) K |
| Wavelength | 1.54178 Å |
| Crystal system | Orthorhombic |
| Space group | P2(1)2(1)2(1) |
| Unit cell dimensions | a = 7.5866(7) Å  α = 90°. |
|  | b = 13.5045(11) Å  β = 90°. |
|  | c = 16.7586(14) Å  γ = 90°. |
| Volume | 1717.0(3) Å³ |
| Z | 4 |
| Density (calculated) | 1.297 Mg/m³ |

Step 2: (R)-6-(1-methyl-1H-indol-5-yl)-3-(3-methyl-2-oxopyrrolidin-3-yl)pyridin-2(1H)-one To a flask was added (R)-3-(2-methoxy-6-(1-methyl-1H-indol-5-yl)pyridin-3-yl)-3-methylpyrrolidin-2-one (534 mg, 1.59 mmol), sodium n-propanethiolate (1287 mg, 13.11 mmol), and DMF (9.5 mL). The mixture was stirred for 17 h at 110° C. Due to incomplete reaction, additional sodium n-propanethiolate (667 mg) was added. The reaction was stirred for 30 h at 110° C. The mixture was diluted with EtOH, concentrated and partitioned between 15% EtOH/DCM and pH 7 phosphate buffer. The aqueous phase was extracted 2× and the combined organic layers were dried over Na₂SO₄ to provide a crude product. Purification by slurrying at r.t. overnight (3.3 mL EtOAc/0.33 mL EtOH) followed by filtration, wash with EtOAc several times and dried under reduced pressure for 3 days at 60-80° C. provided (R)-6-(1-methyl-1H-indol-5-yl)-3-(3-methyl-2-oxopyrrolidin-3-yl)pyridin-2(1H)-one (495 mg, 97%) as a yellow solid. ¹H NMR (600 MHz, methanol-d₄) δ: 1.54 (s, 3H), 1.91-1.98 (m, 1H), 2.68-2.79 (m, 1H), 3.48 (dd, 2H), 3.85 (s, 3H), 6.55 (d, 1H), 6.62 (d, 1H), 7.26 (d, 1H), 7.47 (dd, 1H), 7.49-7.51 (m, 1H), 7.63 (d, 1H), 7.89 (d, 1H); MS (ES+)(M+H) 322.

Example 7

(R)-6-(7-chloro-1-methyl-1H-benzo[d]imidazol-5-yl)-3-(3-methyl-2-oxopiperidin-3-yl)pyridin-2(1H)-one; Tautomer (R)-3-(6-(7-chloro-1-methyl-1H-benzo[d]imidazol-5-yl)-2-hydroxypyridin-3-yl)-3-methylpiperidin-2-one

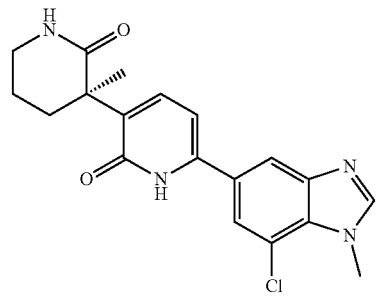 [SMILES: Cn1cnc2cc(-c3ccc([C@@]4(C)CCCNC4=O)c(=O)[nH]3)cc(Cl)c21]

Step 1: (R)-3-(6-(7-chloro-1-methyl-H-benzo[d]imidazol-5-yl)-2-methoxypyridin-3-yl)-3-methylpiperidin-2-one.

To a solution of 5-Bromo-7-chloro-1-methyl-1H-benzo[d]imidazole (1100 mg, 4.48 mmol) in degassed dioxane (2 mL) was added 4,4,4,4',5,5,5',5'-octamethyl-2,2'-bi(1,3,2-dioxaborolane) (1710 mg, 7.72 mmol), PdCl₂(dppf)CH₂Cl₂ (183 mg, 0.224 mmol), and potassium acetate (1760 mg, 17.9 mmol). The vessel was purged with nitrogen then sealed and heated at 110° C. for 1 h. The mixture was then cooled to r.t., and (R)-3-(6-chloro-2-methoxypyridin-3-yl)-3-methylpiperidin-2-one (1140 mg, 4.48 mmol) was added followed by fresh charge of PdCl₂(dppf)CH₂Cl₂ (100 mg). The mixture was heated at 110° C. for 6 h then allowed to cool to r.t. and diluted with ethyl acetate (20 mL). The mixture was filtered through Celite®, and the filtrate was washed with water and brine then dried over MgSO₄. Filtration through a plug of silica and concentration of the filtrate provided the crude title product which was taken onto the demethylation step without purification.

Step 2

To a solution of (R)-3-(6-(7-chloro-1-methyl-1H-benzo[d]imidazol-5-yl)-2-methoxypyridin-3-yl)-3-methylpiperidin-2-one (630 mg, 1.64 mmol) in 5 mL of acetonitrile at r.t. was added sodium iodide (491 mg, 3.27 mmol) followed by chlorotrimethylsilane (0.41 mL, 3.27 mmol). The mixture was stirred for 15 h then the solvent was removed under reduced pressure. The residue was portioned between 15% EtOH: DCM (v/v) and saturated aqueous ammonium chloride. The aqueous phase was extracted three times, and the combined organic layers were washed with 1M aqueous sodium ascorbate solution followed by brine. After filtering and drying over magnesium sulfate, the solvent was removed, and the residue was purified by column chromatography (0-25% EtOH:DCM) to provide Example 7 as a white powder (211 mg, 35%).

¹H NMR (400 MHz. DMSO-d₆) δ ppm 1.41-1.45 (m, 2H) 1.46 (s, 3 H) 2.22-2.45 (m, 2 H) 3.18 (d, 2 H) 4.11 (s, 3 H) 7.23-7.27 (m, 2 H) 7.38 (d, 1 H) 8.02 (br. s., 1 H) 8.32 (s, 2 H) 11.70 (br. s., 1 H). MS (ES+)(M+H) 371.

The compounds listed in the Table 3 below were prepared using analogous conditions to those described above for the preparation of Examples 1 to 7 using the appropriate starting materials.

TABLE 3

| Example | Compound Name | Chemical Structure | ¹H NMR δ | MS |
|---|---|---|---|---|
| 8 | (R)-6-(4-chloro-1-methyl-1H-indazol-6-yl)-3-(3-methyl-2-oxopyrrolidin-3-yl)pyridin-2(1H)-one | 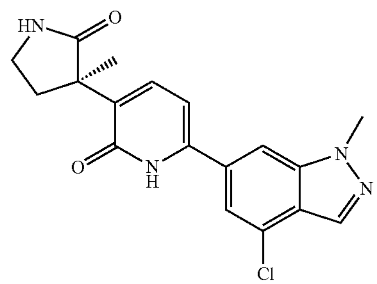 [SMILES: Cn1ncc2c(Cl)cc(-c3ccc([C@@]4(C)CCNC4=O)c(=O)[nH]3)cc21] | CD₃OD: 8.13 (s, 1H), 7.91 (s, 1H), 7.68 (d, 1H), 7.51 (s, 1H), 6.76 (d, 1H), 4.17 (s, 3H), 3.50 (m, 2H), 2.76 (m, 1H), 1.98 (m, 1H), 1.58 (s, 3H) | 357 |
| 9 | (R)-6-(7-fluoro-1-methyl-1H-indol-5-yl)-3-(3-methyl-2-oxopyrrolidin-3-yl)pyridin-2(1H)-one | 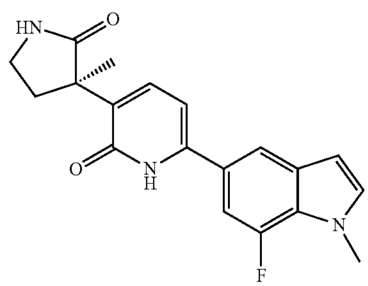 [SMILES: Cn1ccc2cc(-c3ccc([C@@]4(C)CCNC4=O)c(=O)[nH]3)cc(F)c21] | CD₃OD: 7.71 (s, 1H), 7.64 (d, 1H), 7.26 (d, 1H), 7.22 (d, 1H), 6.63 (d, 1H), 6.59 (dd, 1H), 4.04 (s, 3H), 3.49 (m, 2H), 2.74 (m, 1H), 1.97 (m, 1H), 1.56 (s, 3H) | 340 |
| 10 | (R)-6-(1-ethyl-1H-indol-6-yl)-3-(3-methyl-2-oxopyrrolidin-3-yl)pyridin-2(1H)-one | 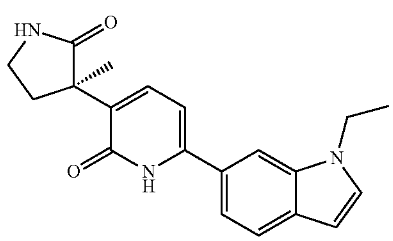 [SMILES: CCn1ccc2ccc(-c3ccc([C@@]4(C)CCNC4=O)c(=O)[nH]3)cc21] | CD₃OD: 7.77 (s, 1H), 7.68 (m, 1H), 7.66 (d, 1H), 7.39 (d, 1H), 7.35 (m, 1H), 6.70 (d, 1H), 6.51 (d, 1H), 4.32 (q, 2H), 3.49 (m, 2H), 2.76 (m, 1H), 1.96 (m, 1H), 1.57 (s, 3H), 1.50 (t, 3H) | 336 |
| 11 | (R)-6-(4-fluoro-1-methyl-1H-indazol-6-yl)-3-(3-methyl-2-oxopiperidin-3-yl)pyridin-2(1H)-one | 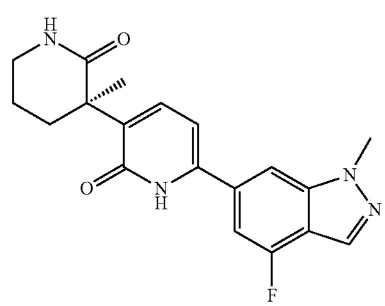 [SMILES: Cn1ncc2c(F)cc(-c3ccc([C@@]4(C)CCCNC4=O)c(=O)[nH]3)cc21] | d6-DMSO: 11.66 (br.s, 1H), 8.22 (s, 1H), 8.02 (s, 1H), 7.43 (d, 1H), 7.35 (d, 1H), 7.28 (d, 1H), 6.76 (br.s, 1H), 4.13 (s, 3H), 3.29 (m, 2H), 2.36 (m, 1H), 1.84 (m, 1H), 1.71 (m, 1H), 1.47 (s, 3H), 1.41 (m, 1H) | 335 |

TABLE 3-continued

| Example | Compound Name | Chemical Structure | $^1$H NMR δ | MS |
|---|---|---|---|---|
| 12 | (R)-6-(1,4-dimethyl-1H-indazol-6-yl)-3-(3-methyl-2-oxopiperidin-3-yl)pyridin-2(1H)-one | 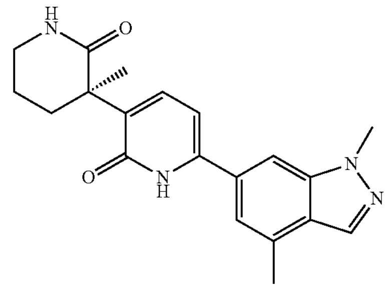 [SMILES: Cc1cc(-c2ccc([C@@]3(C)CCCNC3=O)c(=O)[nH]2)cc2c1cnn2C] | d6-DMSO: 11.62 (br.s, 1H), 8.14 (s, 1H), 7.91 (s, 1H), 7.41 (d, 1H), 7.28 (m, 2H), 6.65 (br.s, 1H), 4.08 (s, 3H), 3.29 (m, 1H), 3.17 (m, 1H), 2.60 (s, 3H), 2.35 (m, 1H), 1.84 (m, 1H), 1.69 (m, 1H), 1.47 (s, 3H), 1.41 (m, 1H) | 351 |
| 13 | (R)-6-(1-ethyl-4-methyl-1H-indazol-6-yl)-3-(3-methyl-2-oxopyrrolidin-3-yl)pyridin-2(1H)-one | 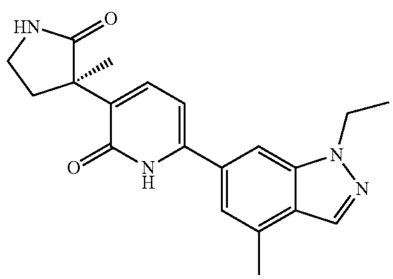 [SMILES: CCn1ncc2c(C)cc(-c3ccc([C@@]4(C)CCNC4=O)c(=O)[nH]3)cc21] | CD$_3$OD: 8.12 (s, 1H), 7.73 (s, 1H), 7.66 (d, 1H), 7.23 (s, 1H), 6.71 (d, 1H), 4.51 (q, 2H), 3.48 (m, 2H), 2.74 (m, 1H), 2.66 (s, 3H), 1.96 (m, 1H), 1.55 (s, 3H), 1.50 (t, 3H) | 351 |
| 14 | (R)-6-(3-cyclopropyl-7-fluoro-1H-indazol-5-yl)-3-(3-methyl-2-oxopiperidin-3-yl)pyridin-2(1H)-one | 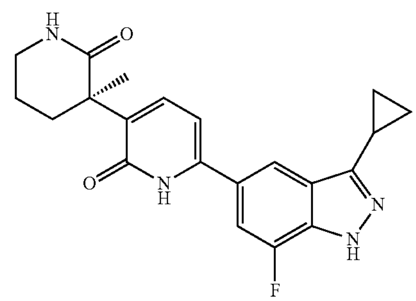 [SMILES: C[C@]1(c2ccc(-c3cc(F)c4[nH]nc(C5CC5)c4c3)[nH]c2=O)CCCNC1=O] | CD$_3$OD: 7.94 (s, 1H), 7.63 (d, 1H), 7.43 (d, 1H), 6.65 (d, 1H), 3.51 (td, 1H), 3.34 (m, 1H), 2.41 (td, 1H), 2.32 (m, 1H), 2.02 (m, 1H), 1.84 (m, 1H), 1.62 (s, 3H), 1.56 (m, 1H), 1.08, (m, 4H) | 381 |

Tautomers of Examples 8 to 13 are as follows, respectively:

Example 8: (R)-3-(6-(4-chloro-1-methy-1H-indazol-6-yl)-2-hydroxypyridin-3-yl)-3-methylpyrrolidin-2-one.

Example 9: (R)-3-(6-(7-fluoro-1-methyl-1H-indol-5-yl)-2-hydroxypyridin-3-yl)-3-methylpyrrolidin-2-one.

Example 10: (R)-3-(6-(1-ethyl-1H-indol-6-yl)-2-hydroxypyridin-3-yl)-3-methylpyrrolidin-2-one.

Example 11: (R)-3-(6-(4-fluoro-1-methyl-1H-indazol-6-yl)-2-hydroxypyridin-3-yl)-3-methylpiperidin-2-one.

Example 12: (R)-3-(6-(1,4-dimethyl-1H-indazol-6-yl)-2-hydroxypyridin-3-yl)-3-methylpiperidin-2-one.

Example 13: (R)-3-(6-(1-ethyl-4-methyl-1H-indazol-6-yl)-2-hydroxypyridin-3-yl)-3-methylpyrrolidin-2-one.

Example 14 has 3 tautomers:

(R)-6-(3-cyclopropyl-7-fluoro-2H-indazol-5-yl)-3-(3-methyl-2-oxopiperidin-3-yl)pyridin-2(1H)-one (R)-3-(6-(3-cyclopropyl-7-fluoro-1H-indazol-5-yl)-2-hydroxypyridin-3-yl)-3-methylpiperidin-2-one.

(R)-3-(6-(3-cyclopropyl-7-fluoro-2H-indazol-5-yl)-2-hydroxypyridin-3-yl)-3-methylpiperidin-2-one.

EP3 Radioligand SPA Binding Assay

To measure the ability of test compounds in the present invention to bind to the human EP3 receptor, and therefore have the potential to antagonize PGE2 activity, radioligand displacement assays were performed. Compound affinity was expressed as a $K_i$ value, defined as the concentration of compound required to decrease [$^3$H] PGE2 binding by 50% for a specific membrane batch at a given concentration of radioligand.

Test compounds were half log serially diluted in 100% DMSO (J. T. Baker #922401). 1 μL of each compound was added to appropriate wells of a 384-well plate (Matrix Cat #4322). Unlabeled PGE2 (Tocris Cat #2296) at a final concentration of 1 μM was used to determine non-specific binding. 1 μL of 100% DMSO (J. T. Baker #922401) was used to determine total binding. Millipore EP3 Chem1 membranes (prepared in-house from cell paste derived from the Millipore ChemiSCREEN™ Human Recombinant EP3 Prostanoid Receptor Calcium-Optimized Stable Cell Line (Millipore Cat #HTS092C. http://www.millipore.com/catalogue/item/hts092c)) were thawed and diluted in binding buffer (50 mM Hepes pH 7.4 (Lonza Cat #17-737), 5 mM MgCl$_2$ (Sigma-M1028), and 0.1% BSA (Sigma A-7409)) to a final concentration of 1 μg/25 μL. 25 μL of diluted membranes were added to prepared compound plates. WGA coated PVT SPA Beads (Perkin Elmer Cat #RPNQ0060) were diluted in binding buffer to a concentration of 4 μg/ul, and 25 μL of the SPA bead mixture was then added to each well for a final assay concentration of 100 μg/well. [³H]-PGE2 (Perkin Elmer Cat #NET428) was diluted in binding buffer to a concentration of 3.375 pM, and 25 μL was added to all wells for a final assay concentration of 1.125 nM. Plates were incubated for 30 minutes at r.t. (approximately 25° C.) with shaking. Radioactivity associated with each well was measured after a 10 hour incubation using a Wallac Trilux MicroBeta plate-based scintillation counter and a normalized protocol at 1 minute read/well. The $K_d$ for [³H]-PGE2 was determined by carrying out saturation binding, with data analysis by non-linear regression, fit to a one-site hyperbola (Graph Pad Prism). $IC_{50}$ determinations were made from competition curves, analyzed with a proprietary curve fitting program (SIGHTS) and a 4-parameter logistic dose response equation. Ki values were calculated from $IC_{50}$ values, using the Cheng-Prusoff equation.

Table 4 below provides the Ki values of Examples for the binding affinity against human EP3 in accordance with the above-described assay. Results are reported as geometric mean Ki values.

TABLE 4

| BIOLOGICAL DATA | | |
| --- | --- | --- |
| Example | Human EP3 Ki [nM] | N |
| 1 | 2.0 | 17 |
| 2 | 3.6 | 4 |
| 3 | 9.5 | 13 |
| 4 | 11.2 | 6 |
| 5 | 12.2 | 25 |
| 6 | 46.0 | 34 |
| 7 | 7.8 | 10 |
| 8 | 14.2 | 5 |
| 9 | 11.9 | 5 |
| 10 | 19.9 | 5 |
| 11 | 13.9 | 5 |
| 12 | 25.0 | 5 |
| 13 | 31.6 | 5 |
| 14 | 29.2 | 5 |

Other features and advantages of this invention will be apparent from this specification and the claims which describe the invention. It is to be understood that both the detailed description is exemplary only and not restrictive of the invention as claimed.

All patents, patent applications and references referred to herein are hereby incorporated by reference in their entirety.

What is claimed is:

1. A compound of Formula I:

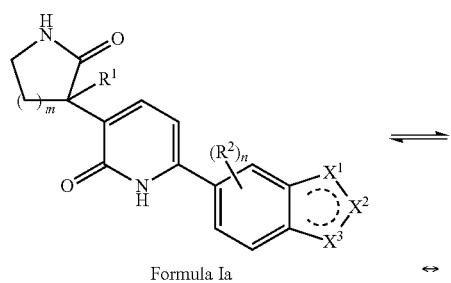

Formula Ia ↔

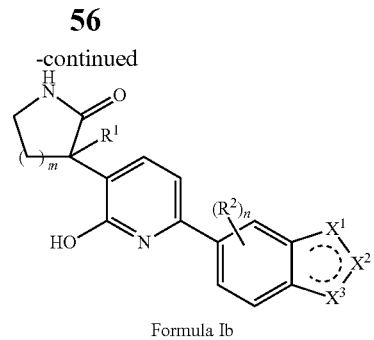

Formula Ib wherein $R^1$ is H, $C_{1-6}$alkyl, or $C_{3-6}$cycloalkyl;

m is 1 or 2;

Each $R^2$ is independently halogen, $C_{1-6}$alkyl, or $C_{3-6}$cycloalkyl;

n is 0 or 1;

$X^1$, $X^2$, and $X^3$ are independently =N—, —NR$^{Xn}$—, or =CR$^{Xc}$—, provided that at least 1 but no more than 2 of $X^1$, $X^2$, and $X^3$ are independently =N— or —NR$^{Xn}$—;

$R^{Xn}$ is H, $C_{1-6}$alkyl, or $C_{3-6}$cycloalkyl; and

Each $R^{Xc}$ is independently H, halogen, $C_{1-6}$alkyl, or $C_{3-6}$cycloalkyl;

or a pharmaceutically acceptable salt thereof.

2. The compound of claim 1, wherein $R^1$ is H, or $C_{1-3}$alkyl;

n is 0 or 1;

$R^2$ is F, Cl, or $C_{1-3}$alkyl;

$R^{Xn}$ is H, or $C_{1-3}$alkyl; and

Each $R^{Xc}$ is H;

or a pharmaceutically acceptable salt thereof.

3. The compound of claim 1, wherein $X^1$, $X^2$, and $X^3$ are independently =N—, —NR$^{Xn}$—, or =CR$^{Xc}$— to provide

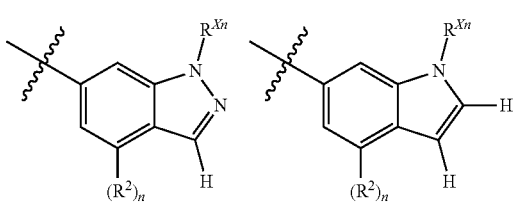

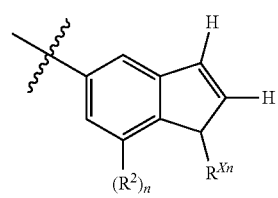

and wherein n is 0 or 1;

$R^2$ is F, Cl, or $CH_3$; and $R^{Xn}$ is $CH_3$ or $CH_2CH_3$;

or a pharmaceutically acceptable salt thereof.

4. The compound of claim 1, wherein the compound is
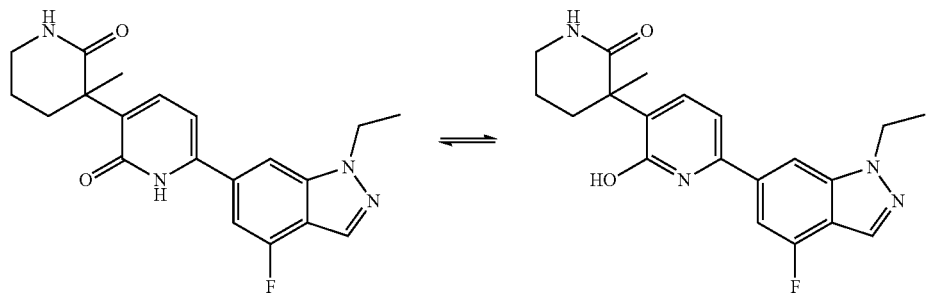
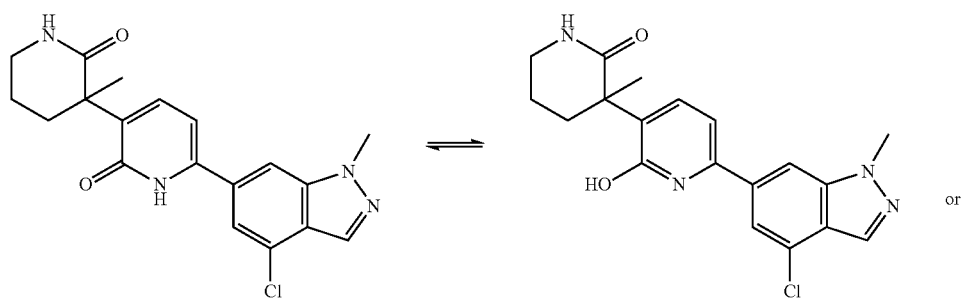 or
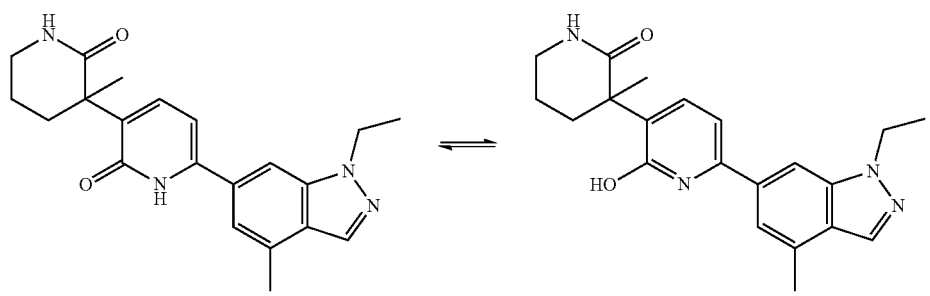
or a pharmaceutically acceptable salt thereof.
5. The compound of claim 4, wherein the compound is
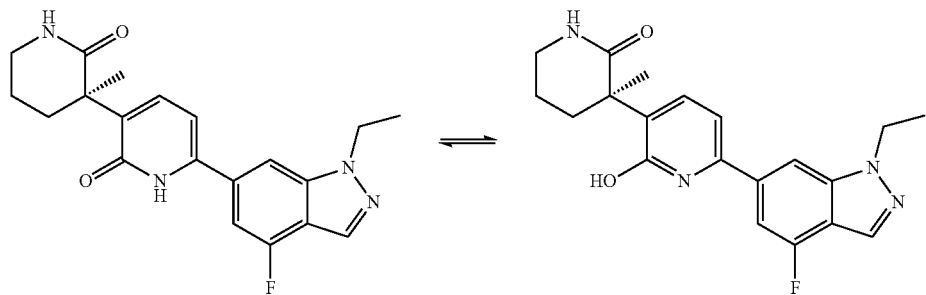

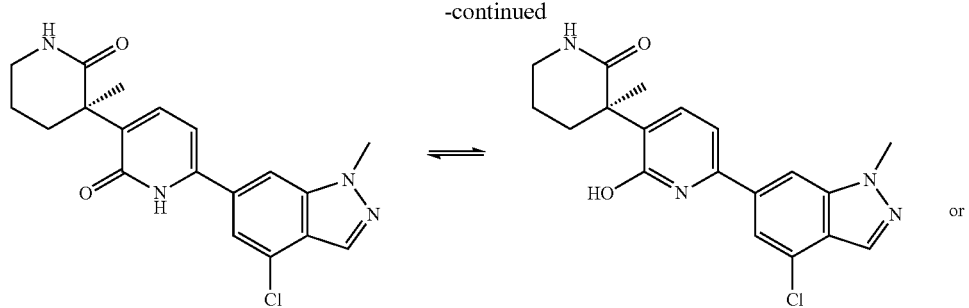
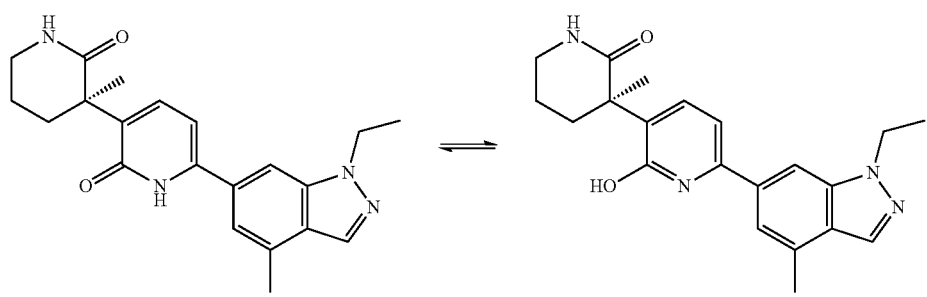
or a pharmaceutically acceptable salt thereof.
6. The compound of claim 1, wherein the compound is
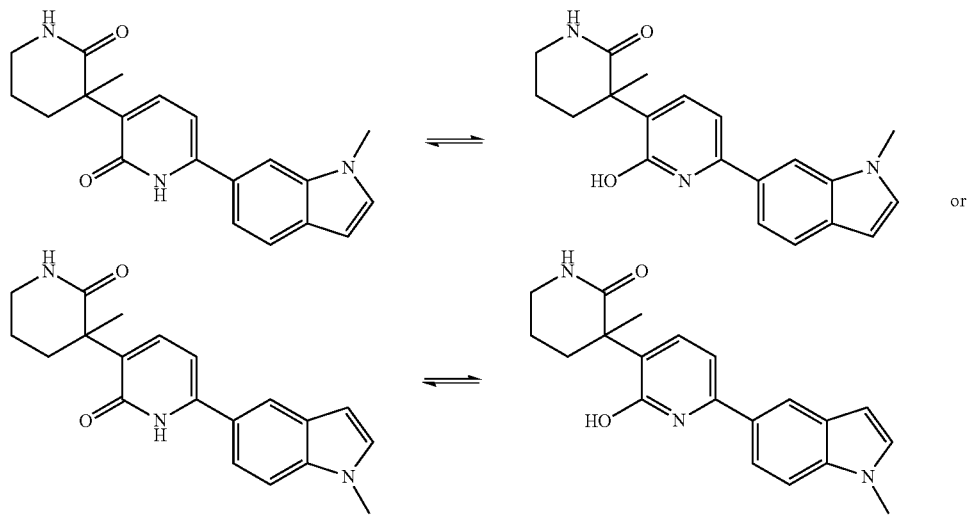
or a pharmaceutically acceptable salt thereof.
7. The compound of claim 6, wherein the compound is
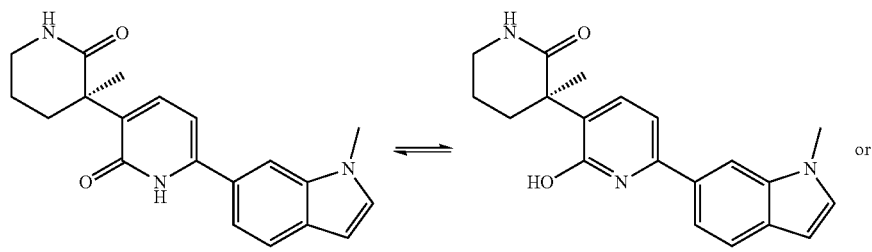

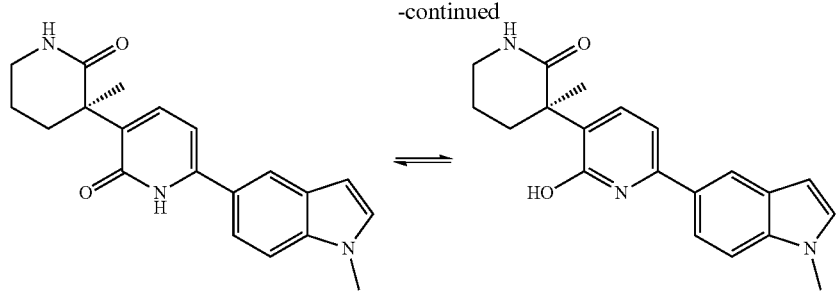

or a pharmaceutically acceptable salt thereof.

8. The compound of claim 1, wherein the compound is

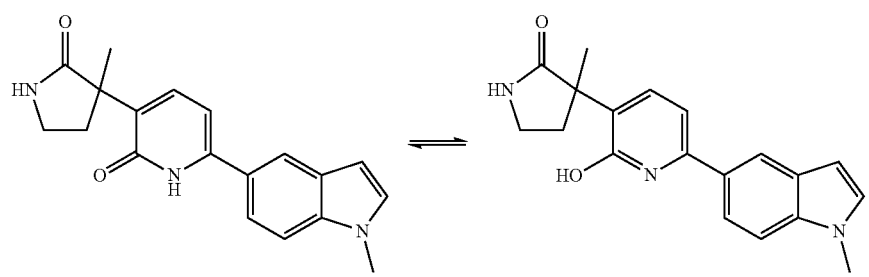 [SMILES: Cn1ccc2cc(-c3ccc(C4(C)CCNC4=O)c(=O)[nH]3)ccc21 ; Cn1ccc2cc(-c3ccc(C4(C)CCNC4=O)c(O)n3)ccc21]

or a pharmaceutically acceptable salt thereof.

9. The compound of claim 8, wherein the compound is

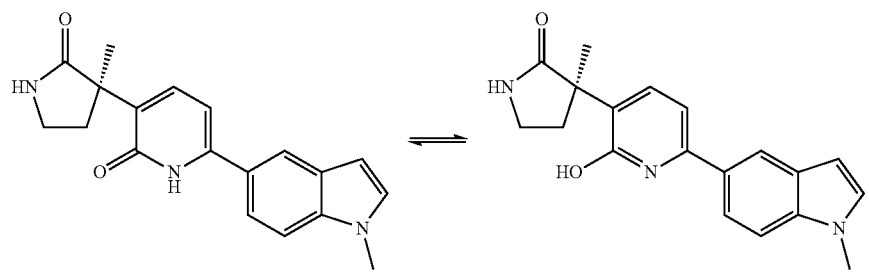 [SMILES: Cn1ccc2cc(-c3ccc([C@@]4(C)CCNC4=O)c(=O)[nH]3)ccc21 ; Cn1ccc2cc(-c3ccc([C@@]4(C)CCNC4=O)c(O)n3)ccc21]

or a pharmaceutically acceptable salt thereof.

10. A compound of Formula I, wherein the compound is
(R)-6-(1-ethyl-4-fluoro-1H-indazol-6-yl)-3-(3-methyl-2-oxopiperidin-3-yl)pyridin-2(1H)-one; or
(R)-3-(6-(1-ethyl-4-fluoro-1H-indazol-6-yl)-2-hydroxypyridin-3-yl)-3-methylpiperidin-2-one; or a pharmaceutically acceptable salt thereof.

11. A compound of Formula I, wherein the compound is
(R)-6-(4-chloro-1-methyl-1H-indazol-6-yl)-3-(3-methyl-2-oxopiperidin-3-yl)pyridin-2(1H)-one;
(R)-3-(6-(4-chloro-1-methyl-1H-indazol-6-yl)-2-hydroxypyridin-3-yl)-3-methylpiperidin-2-one;
(R)-6-(1-ethyl-4-methyl-1H-indazol-6-yl)-3-(3-methyl-2-oxopiperidin-3-yl)pyridin-2(1H)-one; or
(R)-3-(6-(1-ethyl-4-methyl-1H-indazol-6-yl)-2-hydroxypyridin-3-yl)-3-methylpiperidin-2-one; or a pharmaceutically acceptable salt thereof.

12. A pharmaceutical composition comprising the compound of Formula I of claim 1, or a pharmaceutically acceptable salt thereof, and a pharmaceutically acceptable excipient.

13. A pharmaceutical composition comprising the compound of Formula I of claim 10, or a pharmaceutically acceptable salt thereof, and a pharmaceutically acceptable excipient.

14. A pharmaceutical composition comprising the compound of Formula I of claim 11, or a pharmaceutically acceptable salt thereof, and a pharmaceutically acceptable excipient.

* * * * *